(12) United States Patent
Yodfat et al.

(10) Patent No.: US 8,728,034 B2
(45) Date of Patent: May 20, 2014

(54) MODULAR FLUID DELIVERY DEVICE WITH QUICK-RELEASE / CONNECT MECHANISM FOR DRIVE SCREW

(75) Inventors: Ofer Yodfat, Modi'in (IL); Shai Ben-David, Ramat Ishai (IL)

(73) Assignee: Roche Diagnostics Operations Inc., Indianapolis, IN (US)

( * ) Notice: Subject to any disclaimer, the term of this patent is extended or adjusted under 35 U.S.C. 154(b) by 213 days.

(21) Appl. No.: 13/128,608

(22) PCT Filed: Nov. 10, 2009

(86) PCT No.: PCT/IL2009/001052
§ 371 (c)(1),
(2), (4) Date: May 10, 2011

(87) PCT Pub. No.: WO2010/055504
PCT Pub. Date: May 20, 2010

(65) Prior Publication Data
US 2011/0213329 A1  Sep. 1, 2011

Related U.S. Application Data

(60) Provisional application No. 61/113,487, filed on Nov. 11, 2008.

(51) Int. Cl.
*A61M 37/00* (2006.01)
(52) U.S. Cl.
USPC .......................................................... 604/155
(58) Field of Classification Search
USPC ............................. 604/67, 131, 151, 154, 155
See application file for complete search history.

(56) References Cited

U.S. PATENT DOCUMENTS

| 4,498,843 A | 2/1985 | Schneider et al. |
| 5,957,895 A | 9/1999 | Sage et al. |
| 6,248,093 B1 | 6/2001 | Moberg |
| 6,423,035 B1 | 7/2002 | Da et al. |
| 6,485,461 B1 | 11/2002 | Mason et al. |
| 6,589,229 B1 | 7/2003 | Connelly et al. |
| 6,723,072 B2 | 4/2004 | Flaherty et al. |

(Continued)

FOREIGN PATENT DOCUMENTS

| EP | 1 776 975 A2 | 4/2007 |
| WO | WO 2006/121921 A2 | 11/2006 |

(Continued)

OTHER PUBLICATIONS

International Search Report and Written Opinion of the International Search Authority for PCT Application No. PCT/IL2009/001052, Mar. 24, 2010.

*Primary Examiner* — Aarti B Berdichevsky
(74) *Attorney, Agent, or Firm* — Mintz Levin Cohn Ferris Glovsky and Popeo, P.C.

(57) ABSTRACT

Fluid delivery devices and means for engaging components therein are described. The devices may include a plunger positioned within a reservoir and connected to a non-rotating drive screw and a drive nut capable of engagement with the drive screw, where, upon engagement of the drive nut with the drive screw, rotation of the drive nut linearly displaces the drive screw. The devices may also be skin-securable and comprise a reusable part and a disposable part wherein, upon connection of the reusable part and the disposable part, the drive screw engages with the drive nut such that rotation of a motor and/or one or more gears results in rotation of the drive nut and linear displacement of the drive screw.

23 Claims, 17 Drawing Sheets

(56) References Cited

U.S. PATENT DOCUMENTS

| | | |
|---|---|---|
| 6,740,059 B2 | 5/2004 | Flaherty |
| 7,390,314 B2 | 6/2008 | Stutz, Jr. et al. |
| 2003/0130618 A1 | 7/2003 | Gray et al. |
| 2004/0176725 A1 | 9/2004 | Stutz et al. |
| 2005/0238507 A1 | 10/2005 | DiIanni et al. |
| 2007/0106218 A1 | 5/2007 | Yodfat et al. |
| 2007/0191702 A1 | 8/2007 | Yodfat et al. |
| 2008/0051711 A1 | 2/2008 | Mounce et al. |
| 2008/0097327 A1 | 4/2008 | Bente et al. |
| 2008/0214916 A1 | 9/2008 | Yodfat et al. |
| 2008/0215035 A1 | 9/2008 | Yodfat et al. |
| 2010/0217230 A1 | 8/2010 | Yodfat et al. |

FOREIGN PATENT DOCUMENTS

| | | |
|---|---|---|
| WO | WO 2007/052277 | 5/2007 |
| WO | WO 2008/012817 | 1/2008 |
| WO | WO 2008/078318 | 7/2008 |
| WO | WO 2008/139458 | 11/2008 |
| WO | WO 2009/013736 | 1/2009 |
| WO | WO 2009/016636 | 2/2009 |
| WO | WO 2009/113060 | 9/2009 |
| WO | WO 2009/125398 | 10/2009 |
| WO | WO 2010/041260 | 4/2010 |

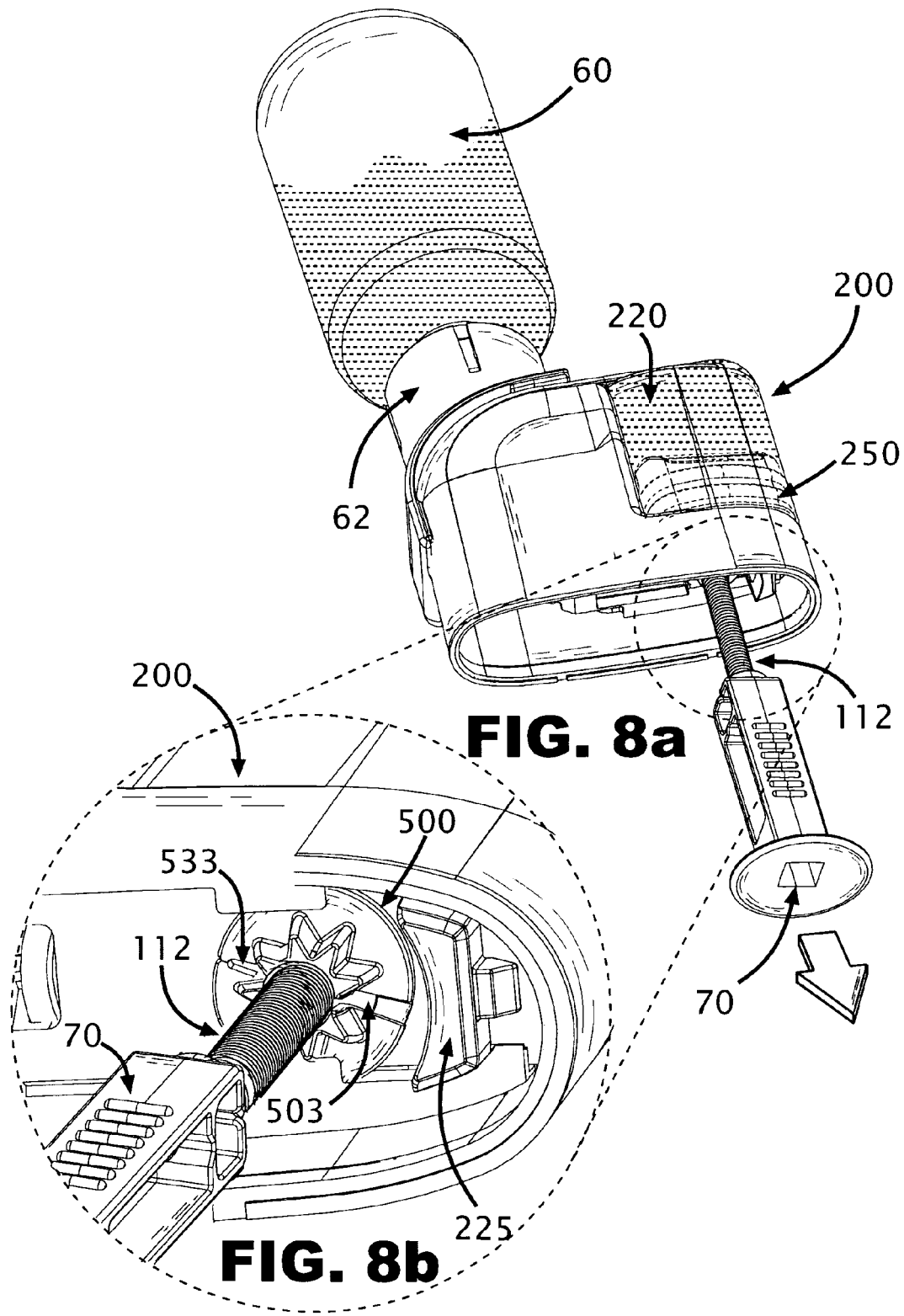

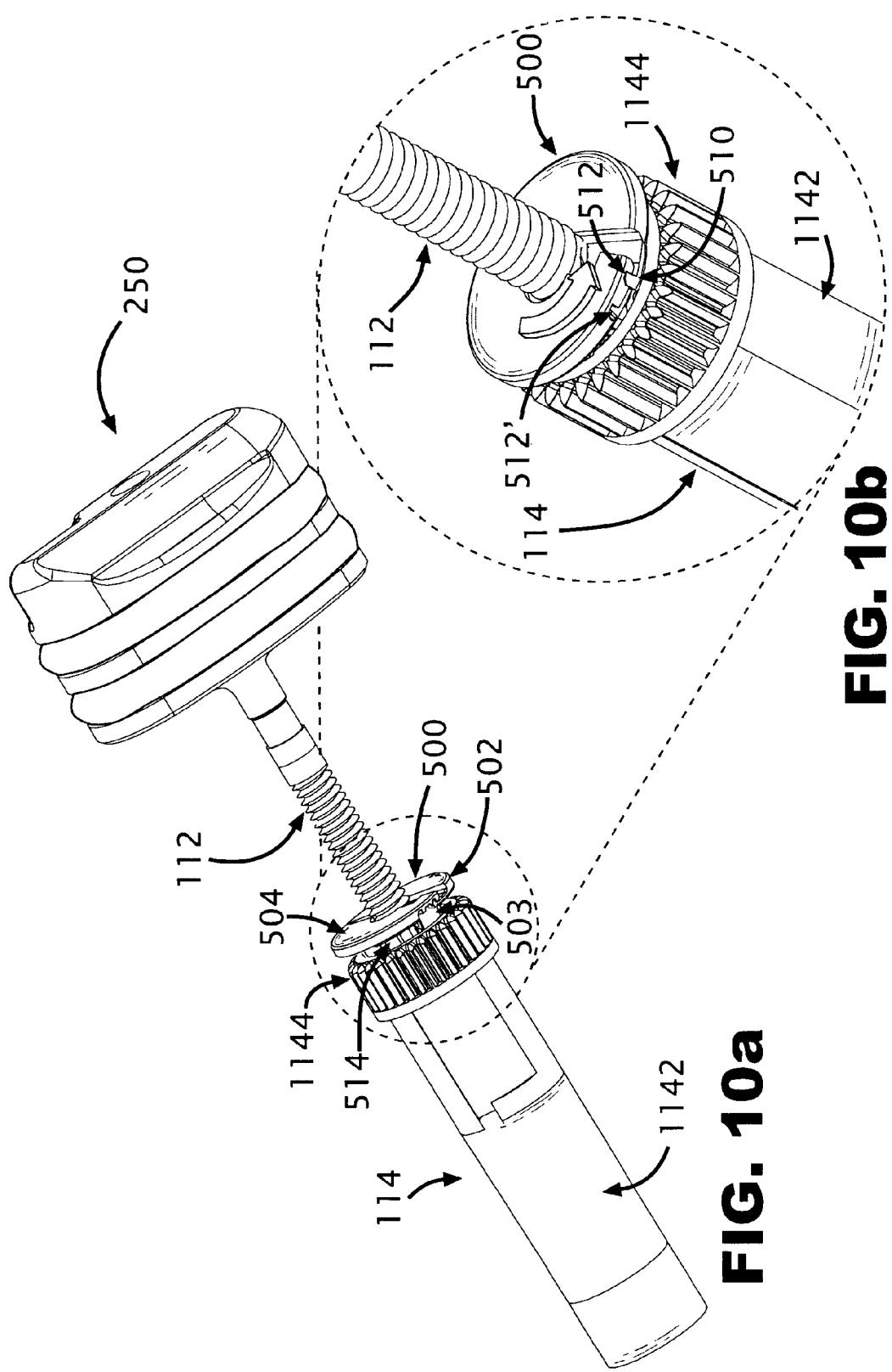

MODULAR FLUID DELIVERY DEVICE WITH QUICK-RELEASE / CONNECT MECHANISM FOR DRIVE SCREW

CROSS-REFERENCE TO RELATED APPLICATIONS

The present application is a 35 U.S.C. §371 national stage entry of PCT/IL2009/001052, which has an international filing date of Nov. 10, 2009 and claims priority to U.S. Provisional Patent Application No. 61/113,487, filed on Nov. 11, 2008 and entitled "Infusion Device and Means for Engagement Reusable and Disposable Part," both disclosures of which are incorporated herein by reference in their entirety.

FIELD

Devices for sustained delivery of fluids and/or analyte sensing are provided. More particularly, fluid delivery devices that include a two-part skin-securable unit having a reusable part and a disposable part are described herein. Even more particularly, a two-part skin-securable fluid delivery device and means for engaging components contained within the device upon connection of the two parts are also provided.

BACKGROUND

Medical treatment of several illnesses requires continuous drug infusion into various body compartments, such as subcutaneous and intra-venous injections. Diabetes mellitus (DM) patients, for example, require the administration of varying amounts of insulin throughout the day to control their blood glucose levels. In recent years, ambulatory portable insulin infusion pumps have emerged as a superior alternative to multiple daily syringe injections of insulin, initially for Type 1 diabetes patients and consecutively for Type 2 diabetes patients. These pumps, which deliver insulin at a continuous basal rate as well as in bolus volumes, were developed to liberate patients from repeated self-administered injections and allow them to maintain a near-normal daily routine. Both basal and bolus volumes must be delivered in precise doses, according to individual prescriptions, since an overdose or under-dose of insulin could be fatal.

The first generation of portable insulin pumps involves a "pager-like" device with a reservoir contained within a housing. The reservoir is typically a syringe barrel and drug is delivered by a continuous forward motion of a plunger within the barrel. Examples of such devices are disclosed in U.S. Pat. Nos. 6,248,093 and 7,390,314. In a typical configuration known in the art, a motor rotates a gear that rotates a drive screw. The plunger is comprised of a proximal end ("plunger head" or "piston head") that contains gaskets and an elongated member shaped like a longitudinal segment of a cylinder ("plunger member") which is internally threaded so that it is inserted into a position of engagement with the drive screw. The drive screw is a threaded screw gear having a diameter that meshes with the internal threads of the plunger member. Thus the motor rotates the drive screw, which engages the threads of the plunger member to displace the plunger in a linear direction. One skilled in the art will understand that the "plunger member" with internal threads is basically a plunger nut. Rotating the drive screw within the plunger nut converts the rotational motion of the drive screw into linear motion of the plunger. While these first generation "pager-like" devices represent a significant improvement over multiple daily injections, they suffer major drawbacks, including large size and weight and long tubing.

To avoid such limitations, a new concept was proposed and implemented in second generation pumps. The new concept concerns a remote-controlled skin-adherable device having a bottom surface adapted to be in contact with the patient's skin. A reservoir is contained within the housing and reservoir filling is done with an additional syringe that is used to draw the drug from a vial with an injection needle that is also adapted for fluid communication with the reservoir. This paradigm was discussed, for example, in U.S. Pat. Nos. 4,498,843, 5,957,895, 6,589,229, 6,740,059, 6,723,072 and 6,485,461. These second generation skin-adherable devices also have drawbacks, the most significant being that the entire device, including all the expensive components (e.g., electronics and driving mechanism), must be disposed every 2-3 days due to, for example, insertion site infections and reduced insulin absorption.

A typical driving mechanism of a second generation, skin-adherable pump is described in U.S. Published Patent Application No. 2005/0238507 assigned to Insulet Corporation. Insulet's device has a plunger rigidly connected to a non-rotating threaded drive screw and is coupled to a drive wheel that includes a thread-engaging mechanism that moves from a non-thread-engaging position to a thread-engaging position. The non-thread-engaging position allows the threaded drive screw to pass freely through the drive wheel when the reservoir is being filled. The thread-engaging position allows the threaded drive screw to be advanced when the drive wheel is rotated.

Third generation skin-securable devices were devised to avoid the cost issues (e.g., disposing expensive components every 2-3 days) of the second generation devices and to extend patient customization. An example of such a device is described in co-owned U.S. patent application Ser. No. 11/397,115 (Publication No. 2007/0106218), filed Apr. 3, 2006 and entitled "Systems and Methods for Sustained Medical Infusion and Devices Related Thereto" and International Patent Application No. PCT/IL06/001276 (Publication No. WO/2007/052277), filed May 11, 2006 and entitled "Modular Portable Infusion Pump." This third generation device contains a remote control unit and a skin-securable (e.g., adherable) unit (e.g., "patch unit") that includes two parts: (1) a reusable part containing the electronics, at least a portion of the driving mechanism and other relatively expensive components, and (2) a disposable part containing the reservoir.

A skin-securable fluid (e.g., insulin) delivery device was also disclosed in co-owned U.S. patent application Ser. No. 11/989,681 and International Patent Application No. PCT/IL07/000,932 (Publication No. WO/2008/012817), both filed Jul. 24, 2007, claiming priority to U.S. Provisional Patent Application Nos. 60/833,110 filed Jul. 24, 2006 and 60/837,877 filed Aug. 14, 2006, and entitled "Systems, Devices, and Methods for Fluid/Drug Delivery," the content of all of which is incorporated herein by reference in its entirety.

A typical driving mechanism of a third generation skin-securable pump is described in U.S. Published Patent Application No. 2008/0097327 assigned to Medtronic MiniMed. The disposable part in this pump includes a plunger having a rigidly-connected drive screw. The reusable part contains a motor and a gear that comprises a driving wheel. Upon connection of reusable and disposable parts, the drive screw is engaged with the drive wheel. Rotation of the drive wheel is converted to linear motion of the drive screw.

A fourth generation infusion device has been devised as a dispensing unit that can be disconnected from and reconnected to a skin-securable cradle unit and can be operated by buttons located on the reusable part. This fourth generation device is disclosed in the following co-owned applications:

(i) U.S. patent application Ser. No. 12/004,837 (Publication No. 2008/0215035) and International Patent Application No. PCT/IL07/001578 (Publication No. WO2008/078318), both filed Dec. 20, 2007, claiming priority to U.S. Provisional Patent Application No. 60/876,679 filed Dec. 22, 2006, and entitled "Systems, Devices, and Methods for Sustained Delivery of a Therapeutic Fluid," (ii) International Patent Application No. PCT/IL08/001001 (Publication No. WO2009/013736), filed Jul. 20, 2008, claiming priority to U.S. Provisional Patent Application No. 60/961,527 and entitled "Manually Operable Portable Infusion Pump" and (iii) International Patent Application No. PCT/IL08/001057 (Publication No. WO2009/016636), filed Jul. 31, 2008, claiming priority to U.S. Provisional Application Nos. 60/963,148 and 61/004,019, and entitled "Portable Infusion Device with Means for Monitoring and Controlling Fluid Delivery," the content of all of which is incorporated herein by reference in its entirety.

The third and fourth generation devices can be used in conjunction with an analyte (e.g., glucose) sensing apparatus to enable continuous readings of analyte levels. Fluid dispensing can be done automatically according to analyte sensing (closed loop system) or semi-automatic if the user wishes to control delivery (open loop system). A fourth generation device with sensing capabilities is disclosed in the co-owned U.S. patent application Ser. Nos. 11/706,606 (Publication No. 2007/0191702), filed Feb. 14, 2007 and entitled "Systems and Methods for Sensing Analyte and Dispensing Therapeutic Fluid," and 11/963,481 (Publication No. 2008/0214916), filed Dec. 21, 2007 and entitled "Fluid Delivery with In Vivo Electrochemical Analyte Sensing," the content of all of which is incorporated herein by reference in its entirety.

A typical pumping mechanism of third and fourth generation two-part skin-securable devices may be a "syringe-like" or "piston-type" pumping mechanism. Here, a plunger (e.g., piston) slides within a reservoir (e.g., barrel) to draw fluid outwardly. The plunger may be pushed forward by a rotating drive screw (plunger rod) that freely articulates within the plunger. Linear motion is achieved by rotation of the drive screw relative to a nut. The nut is rigidly fixed to the housing or chassis (insert) of the disposable part. Rotating the drive screw within the non-rotating nut causes linear motion of the drive screw relative to the nut. The drive screw is also used as a plunger rod to backwardly slide the plunger during reservoir filling. After filling, the disposable part that contains the reservoir and outlet port is connected to the reusable part concomitantly with engagement of the drive screw with the gear of the reusable part.

The major limitation of a freely-articulating rotating drive screw is inaccuracy in drug delivery caused mainly due to plunger wobbling during forward motion within the reservoir. Plunger wobbling is caused by rotation of the distal end of the drive screw at the articulation point within the plunger.

SUMMARY

Devices and means for engaging various components contained within such devices are disclosed herein. Embodiments of the devices are directed to delivering therapeutic fluid into the body of a patient and/or sensing analytes contained within the body of a patient. Such devices may include a pumping mechanism having a reservoir (e.g., a barrel) and a plunger that may be positioned within the reservoir and comprises a proximal end and a distal end. In some embodiments, the plunger distal end may contact fluid contained in the reservoir and, thus, may include one or more gaskets to prevent leakage of the fluid from the reservoir. The plunger's proximal end may have a rigid extension that comprises a drive screw with external threads, according to some embodiments. The drive screw may be rigidly connected to the plunger and unable to rotate relative to the plunger and the reservoir. The drive screw may also have a conical tip or a hat-shaped tip, according to some embodiments.

Some device embodiments may also include a drive nut with internal threads and external teeth. The drive nut may be capable of engagement to, and in some embodiments disengagement from, the drive screw based on engagement between the internal threads of the drive nut and external threads on the drive screw. Some embodiments may also have a drive nut that comprises two parts, namely a first section and a second section (e.g., a split-nut). According to certain embodiments, one or more gaps may exist between the first section and the second section at least when the drive nut is disengaged from the drive screw. When the drive nut is engaged with the drive screw, at least one of the one or more gaps may be narrowed, according to some embodiments. The first section and second section, in certain embodiments, may be connected by a hinge. In some embodiments, the first section may be detachably connectable to the second section, or vice versa. In some embodiments, the drive nut may have at least one latch and one or more corresponding recesses for locking together the first section and the second section. The drive nut may also have a body portion that engages with a receiving portion. Some embodiments of the body portion of the drive nut may be at least partially conical and/or curved. The body portion may also have external teeth that engage with inner teeth of the receiving portion, according to some embodiments. In some embodiments, the receiving portion may be in the reusable portion of a two-part dispensing unit. Some embodiments of the receiving portion may include a gear portion with outer teeth configured to mesh with teeth of one or more gears. The receiving portion may also have an elongated portion, according to some embodiments. The receiving portion may also include at least one of outer teeth and inner teeth. Some embodiments of the device may also have an energy source and an energy detector for detecting a position of the drive screw within the receiving portion. Some embodiments of the drive nut have an "open" position and at least two closed positions. In one closed position, the two parts of the drive nut may be locked together but still maintain relative space between each other (i.e., form a slit therebetween) that can further be closed. In this position, the drive nut and drive screw are said to be "disengaged." In another closed position, the two parts of the drive nut are seated against each other. In this position, the drive nut and the drive screw are said to be "engaged."

To this end, embodiments of the drive nut may have two basic operational modes—disengaged and engaged. In the disengaged mode, the two parts (i.e., the first section and second section) of the drive nut are locked together but there is still space between them (i.e., the slit is open), whereby the drive screw can freely slide backwards and forwards within and relative to the drive nut, according to some embodiments. In the engaged mode, the two parts of the drive nut are seated against each other (i.e., the slit is closed). In this position, the drive nut's internal threads are engaged with the drive screw threads such that upon rotation of the drive nut, the drive screw is linearly displaced. More specifically, because the drive screw is unable to rotate based on its rigid connection with the plunger, the rotational movement of the drive nut is converted to linear movement. Moreover, in some embodiments, the external teeth of the drive nut may be engaged with the motor and/or one or more gears connected to the motor and can be rotated when the motor is operated. In some embodiments, one or more slits may be configured to remain substantially open in the engaged position, in order to provide elasticity to the drive nut. It can be appreciated that these slits do not enable the drive screw to freely slide backwards and forwards within and relative to the drive nut when the drive nut is in the engaged position. In some embodiments, the external teeth of the drive nut may be engaged within a receiving portion that may be tubular in shape (e.g., "rotating sleeve") and may have inner teeth that mesh with the external teeth of the drive nut. When the external teeth of the drive nut hold tight with the inner teeth of the rotating sleeve, rotation of the rotating sleeve causes rotation of the drive nut and ultimately linear displacement of the drive screw, since the drive screw is unable to rotate based on its rigid connection with the plunger.

Some embodiments of the device may comprise a dispensing unit, a skin-securable cradle and a remote control unit. In some embodiments, the dispensing unit may be skin-securable. In some embodiments, the dispensing unit may be referred to as a patch unit due to its structural similarity to a thin patch that can be affixed to the body of a patient. Some embodiments of the dispensing unit may be disconnected from and reconnected to the cradle. A connecting lumen may provide fluid communication between the dispensing unit and a subcutaneous cannula connected to the cradle. In some embodiments, fluid delivery may be remotely controlled by the remote control unit and/or by buttons located on the dispensing unit. The device, according to some embodiments, may have a sensor for continuously sensing one or more body analytes. The device may also have a remote control adapted for at least one of sending and receiving information to and from the device.

The dispensing unit (e.g., a "patch unit") may comprise a pumping mechanism, reservoir and an exit port, according to some embodiments. The dispensing unit may also be configured in some embodiments as a single unit including a reservoir, energy supply (e.g., batteries), electronics and a pumping mechanism, or, in other embodiments, as a two-part unit. Embodiments of the two-part dispensing unit may include a reusable part containing relatively expensive components, such as for example a motor, one or more gears and/or electronics. In some embodiments, the reusable part may include a receiving portion (e.g., a rotating sleeve) driven by at least one of the motor and the one or more gears, wherein the receiving portion is adapted to receive the drive screw and engage with the drive nut. Such engagement of the drive nut with the receiving portion may result in the engagement of the drive nut with the drive screw, according to some embodiments. The two-part dispensing unit may also include a disposable part that contains relatively inexpensive components, such as for example an exit port, a reservoir and/or a plunger. In some embodiments, at least a portion of a disposable part housing may define the reservoir. The disposable part may also have an exit port in fluid communication with the reservoir, wherein the exit port is configured to enable filling of the reservoir with fluid via the exit port by pulling the drive screw with the plunger outwardly from the reservoir when the drive nut is disengaged from the drive screw, according to some embodiments. Some embodiments of the device may include a filling adapter having a first end capable of being coupled to the exit port and a second port capable of being coupled to a fluid container, wherein upon coupling the first end to the exit port and the second port to the fluid container, fluid communication is established between the fluid container and the reservoir. In some embodiments, the plunger may comprise, or be rigidly connected to, a drive screw and may be coupled with a drive nut. Some embodiments of the drive nut may comprise internal threads and/or external teeth. The drive nut may be capable of engagement with the drive screw, according to some embodiments. The external teeth may have a conical and/or curved shape, according to some embodiments. Some embodiments of the drive nut may also include one or more slits. In some embodiments, upon connection of the reusable part and the disposable part, the drive nut may engage with the drive screw such that rotation of at least one of the motor and the one or more gears results in rotation of the drive nut to linearly displace the drive screw and the plunger to deliver fluid contained within the reservoir.

Embodiments of the cradle may comprise a flat sheet with an adhesive layer facing the skin of a patient. Embodiments of the cradle may also contain a passageway to a subcutaneous cannula and snaps to secure the cannula and the dispensing unit to the cradle. Embodiments of the remote control may include a handheld unit for programming fluid flows, controlling the dispensing unit, acquiring data and displaying information. Some embodiments of the remote control may further comprise a wrist-watch, cellular phone, PDA, iPhone, mp3 player (e.g., iPod) and laptop.

Some device embodiments may include a fluid delivery device having a reusable part including a motor and one or more gears, a disposable part including a reservoir and a plunger positioned within the reservoir and connected to a plunger rod, and an engagement member capable of engagement with the plunger rod. In certain embodiments, the engagement member may have a first section and a second section, wherein one or more gaps may exist between the first section and the second section at least when the engagement member is disengaged from the plunger rod, wherein upon connection of the reusable part and the disposable part, the engagement member may engage with the plunger rod such that rotation of at least one of the motor and the one or more gears results in rotation of the engagement member to linearly displace the plunger rod and the plunger to deliver fluid contained within the reservoir.

In some embodiments, fluid delivery from the device may be provided by a piston-type pumping mechanism. According to certain embodiments, the plunger may be moved forward by the linear displacement of the drive screw upon rotation of the drive nut after engagement of the drive nut with the drive screw and one or more gears. The drive screw may also be used to displace the plunger backward within the reservoir to draw in fluid and fill the reservoir when the drive nut is in a disengaged position.

In some embodiments, the reservoir may have a flat profile (e.g., oval, ellipse or four arches) to maintain a thin device configuration.

Upon connecting the reusable part and the disposable part, the drive nut may engage the rotating sleeve of the reusable part, according to some embodiments. Also upon connection, the drive nut may close and cause the threads of the drive nut and the external threads of the drive screw to engage. Rotation of the rotating sleeve may then cause rotation of drive nut and resultantly displace the drive screw and the plunger linearly within reservoir.

It is an object of some embodiments herein to provide a fluid delivery device that may include a reservoir retaining fluid, a plunger positioned within the reservoir and connected to a non-rotating drive screw, and a drive nut capable of engagement with the drive screw. The fluid delivery device may further include a housing to accommodate the reservoir, the plunger, the drive screw and the drive nut. In such embodiments, upon engagement of the drive nut with the drive screw, rotation of the drive nut may linearly displace the drive screw and the plunger connected thereto to deliver fluid from the reservoir.

It is an object of some embodiments herein to provide a device for infusing medical fluids into the body, wherein the device includes a piston-type pumping mechanism composed of a reservoir and a plunger. In such embodiments, the plunger may comprise, or be rigidly connected to, a drive screw coupled with a drive nut via a threaded engagement, whereby rotation of the drive nut results in the linear displacement of the drive screw. Rotation, in such embodiments, may occur upon engagement of the drive nut with one or more gears and/or a motor.

It is another object of some embodiments herein to provide a two-part fluid delivery device having a reusable part and disposable part. In such embodiments, the reusable part may contain a motor, one or more gears, electronics and/or other relatively expensive components and the disposable part may contain relatively inexpensive parts, such as an exit port, a reservoir and a plunger. In some embodiments, an energy supply (e.g., batteries) may reside in the disposable part and/or in the reusable part.

It is another object of some embodiments herein to provide a fluid delivery device for sustained infusion of therapeutic fluid with a controlled rate of injection and/or delivery of fluid into the body of a patient.

It is another object of some embodiments herein to provide a fluid delivery device that is thin in overall configuration (i.e., has a patch-like structure), has no external tubing and can be connected to any part of the body of a patient.

It is another object of some embodiments herein to provide a fluid delivery device for infusing therapeutic fluid into the body of a patient, wherein the device also contains a skin-securable (e.g., skin-adherable) cradle with a passageway for a subcutaneous cannula and snaps for rigidly securing the patch and allowing disconnection and reconnection of the device from and to the cradle.

It is another object of some embodiments herein to provide a fluid delivery device that comprises a dispensing patch unit. In some embodiments of the dispensing patch unit, infusion programming can be carried out by a remote control unit and/or by at least one control button located on the dispensing patch unit.

It is another object of some embodiments herein to provide a device for infusing fluid into the body of a patient through a flexible, soft insertable subcutaneous cannula.

It is another object of some embodiments herein to provide a fluid delivery device that comprises (i) a slidable plunger for moving fluid into and/or out of a reservoir, wherein the plunger is rigidly connected to a non-rotating drive screw and (ii) a drive nut capable of engagement with the drive screw. In some embodiments, upon engagement of the drive nut with the non-rotating drive screw, rotational movement of the drive nut is converted into linear motion and linearly displaces the drive screw and the connected plunger within the reservoir.

It is another object of some embodiments herein to provide a skin-securable fluid delivery device for delivering therapeutic fluid that comprises a (i) reusable part including a motor and a gear and (ii) a disposable part including a reservoir and a plunger for displacing fluid into and/or out of the reservoir. In some embodiments, the plunger may be connected to a drive screw and coupled to a drive nut. Upon connection of the reusable part and the disposable part, the drive screw and the drive nut are engaged, and rotation of the gear results in rotation of the drive nut, which in turn linearly displaces the non-rotating drive screw.

It is another object of some embodiments herein to provide a method for delivering a fluid from a portable fluid delivery device for delivering therapeutic fluid, wherein the method may comprise providing a portable fluid delivery device that comprises a reusable part including a motor and one or more gears and a disposable part including a reservoir. In some method embodiments, the disposable part may include a plunger that is connected to a drive screw and displaces fluid into and/or out of the reservoir. The disposable part further includes a drive nut which may be capable of engagement with the drive screw, where prior to connection of the reusable part and the disposable part, the drive nut is disengaged from the drive screw and allows the drive screw to freely move within the drive nut. Some method embodiments may also include positioning a free end of the drive screw within a receiving portion in the reusable part and connecting the reusable part and the disposable part, wherein, upon connection, the drive nut engages the drive screw and one or more gears such that upon rotation of the drive nut, the drive screw is linearly displaced. In some embodiments, connecting the reusable part with the disposable part may include engaging the drive nut with the receiving portion, wherein, upon engagement, rotation of the receiving portion by at least one of the motor and the one or more gears rotates the drive nut.

Embodiments of such a method may include one or more of the above described features of the device, as well as any of the following features.

It is another object of some embodiments to provide a device that includes a skin-securable fluid dispensing unit that continuously monitors a body analyte (e.g., glucose) levels and can dispense therapeutic fluid (e.g., insulin) according to analyte (e.g., glucose) levels (closed and/or open loop systems). In such embodiments, the dispensing unit may include a piston-type pumping mechanism that comprises a reservoir and a slidable plunger rigidly connected to a drive screw that is coupled to a drive nut, such that rotation of the drive nut linearly displaces the drive screw and the plunger within the reservoir.

It is another object of some embodiments to provide a skin-securable fluid dispensing unit that is miniature, discreet, economical for users and highly cost-effective.

BRIEF DESCRIPTION OF THE DRAWINGS

FIGS. 8*a*-8*b* illustrate the reservoir filling process, according to some embodiments.

FIGS. 10a-10b show a drive screw coupled with a drive nut after engagement with a rotating sleeve, according to some embodiments.

DETAILED DESCRIPTION

Figure 1:
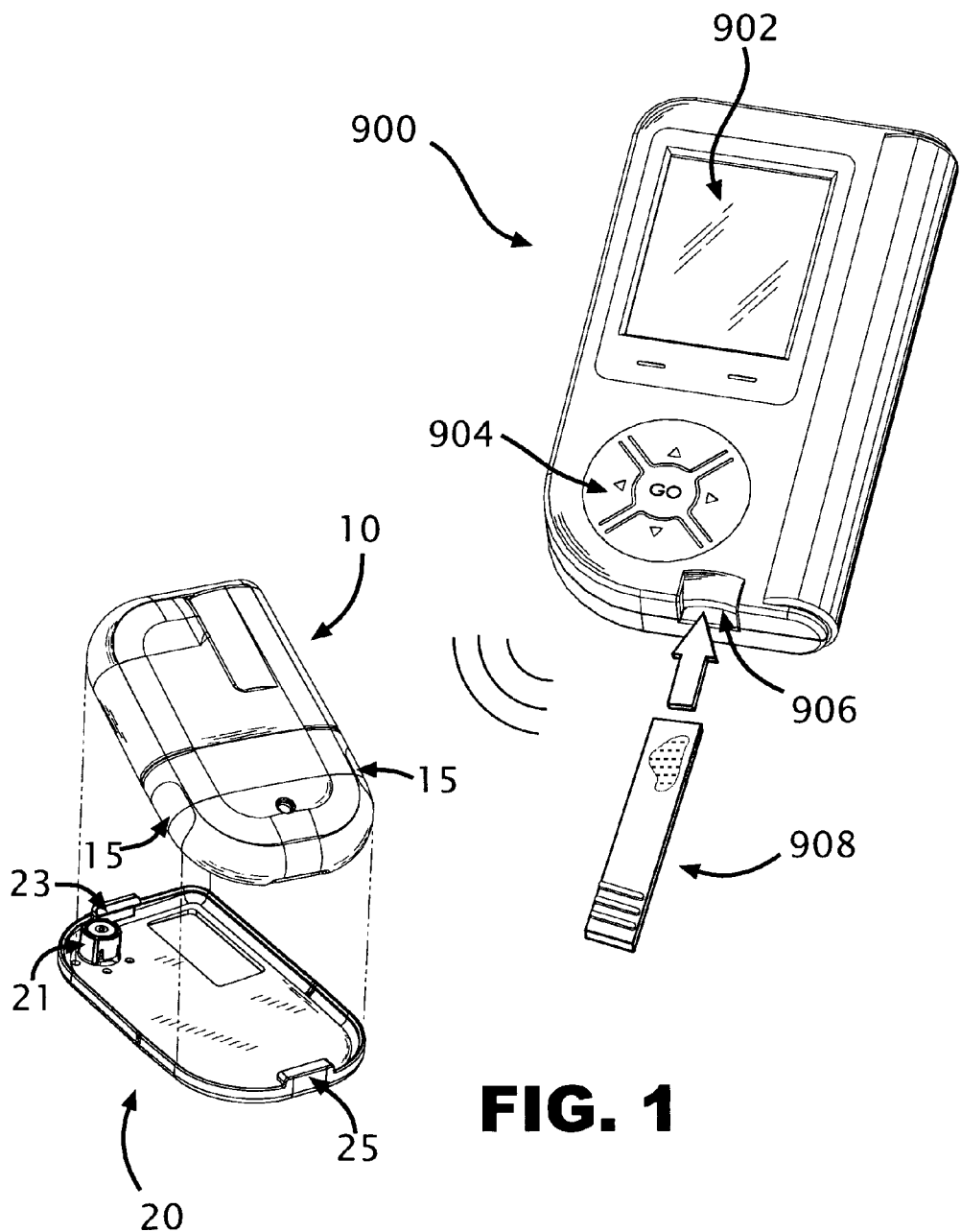
FIG. 1 shows a device comprising a remote control unit containing an integrated blood glucose monitor, a two-part fluid dispensing unit and a skin-securable cradle unit, according to some embodiments.

FIG. 1 shows an infusion device that includes a dispensing unit 10 ("unit") that may be comprised of one or more components. In some embodiments, the unit 10 may be referred to as a patch unit due to its structural similarity to a thin patch that can be affixed to the body of a patient. The unit 10 can be disconnected from and reconnected to a cradle unit 20 (hereinafter "cradle"). The cradle 20 may comprise a substantially flat sheet with a passageway for inserting a cannula into the patient's body therethrough. In some embodiments, the passageway may be defined by a well 21 configured as a protrusion (e.g., a tubular protrusion) emerging upwardly from the substantially flat sheet. The cradle 20 may further include an adhesive at its bottom and one or more connectors 23, 25 (e.g., snaps, latches) to secure the unit 10 to the cradle 20. The well 21 may also comprise connectors (not shown) to secure the cannula (not shown) to the cradle 20. In some embodiments, the cradle 20 may be skin-securable (e.g., skin-adherable). Commands to dispense fluid may be initiated using buttons 15 located on the unit 10, as disclosed, for example, in (i) co-owned International Patent Application No. PCT/IL08/001001 (Publication No. WO2009/013736), filed Jul. 20, 2008, claiming priority to U.S. Provisional Patent Application No. 60/961,527 and entitled "Manually Operable Portable Infusion Pump" and/or (ii) co-owned International Patent Application No. PCT/IL08/001057 (Publication No. WO2009/016636), filed Jul. 31, 2008, claiming priority to U.S. Provisional Patent Application Nos. 60/963,148 and 61/004,019, and entitled "Portable Infusion Device with Means for Monitoring and Controlling Fluid Delivery," the content of all of which is hereby incorporated by reference in its entirety.

FIG. 1 also shows that the infusion device may include a remote control unit 900 (hereinafter "RC"). In some device embodiments, the RC 900 may include an integrated blood glucose monitor. The RC 900 may also include a screen 902, a keypad 904 and a slot 906 to receive a blood test strip 908. In some embodiments, the keypad 904 may contain one or more buttons that allow a user to initiate fluid infusion, e.g., a basal rate or bolus dose of insulin. In some embodiments, determining when to initiate a fluid infusion and what constitutes a proper dose of fluid may be determined based on the sensing of body analytes using an analyte sensor (e.g., a continuous glucose monitor), as referenced herein below. The RC 900 may also be used for programming the unit 10, acquiring data from the unit 10 and/or for communicating with other electronic devices (e.g., a PC) to carry out, for example, data downloading and/or uploading.

Examples of such infusion devices are disclosed in co-owned U.S. patent application Ser. No. 12/004,837 (Publication No. 2008/0215035) and International Patent Application No. PCT/IL07/001578 (Publication No. WO2008/078318), both filed on Dec. 20, 2007, claiming priority to U.S. Provisional Patent Application No. 60/876,679 and entitled "Systems, Devices, and Methods for Sustained Delivery of a Therapeutic Fluid," the content of all of which is hereby incorporated by reference in its entirety. Further examples are also disclosed in co-owned U.S. patent application Ser. No. 11/397,115 (Publication No. 2007/0106218) filed Apr. 3, 2006 and entitled "Systems and Methods for Sustained Medical Infusion and Devices Related Thereto," International Patent Application No. PCT/IL06/001276 (Publication No. WO/2007/052277) filed Nov. 5, 2006 and entitled "Modular Portable Infusion Pump" and International Patent Application No. PCT/IL09/000388 (Publication No. WO2009/125398), filed Apr. 7, 2009, claiming priority to U.S. Provisional Patent Application No. 61/123,509 and entitled "Systems, Devices and Methods for Fluid Delivery," the content of all of which is hereby incorporated by reference in its entirety.

Also, co-owned U.S. patent application Ser. Nos. 11/706,606 (Publication No. 2007/0191702) filed Feb. 14, 2007 and entitled "Systems and Methods for Sensing Analyte and Dispensing Therapeutic Fluid" and 11/963,481 (Publication No. 2008/0214916) filed Dec. 21, 2007 and entitled "Fluid Delivery With In Vivo Electrochemical Analyte Sensing," the content of which is hereby incorporated by reference in its entirety, disclose device embodiments that include a dispensing unit (e.g., an insulin dispensing patch) and an analyte sensor (e.g., a continuous glucose monitor). This type of dual function device has a similar configuration to the unit 10 outlined above and can also be disconnected and reconnected from and to the skin at a patient's discretion.

Figure 2A:
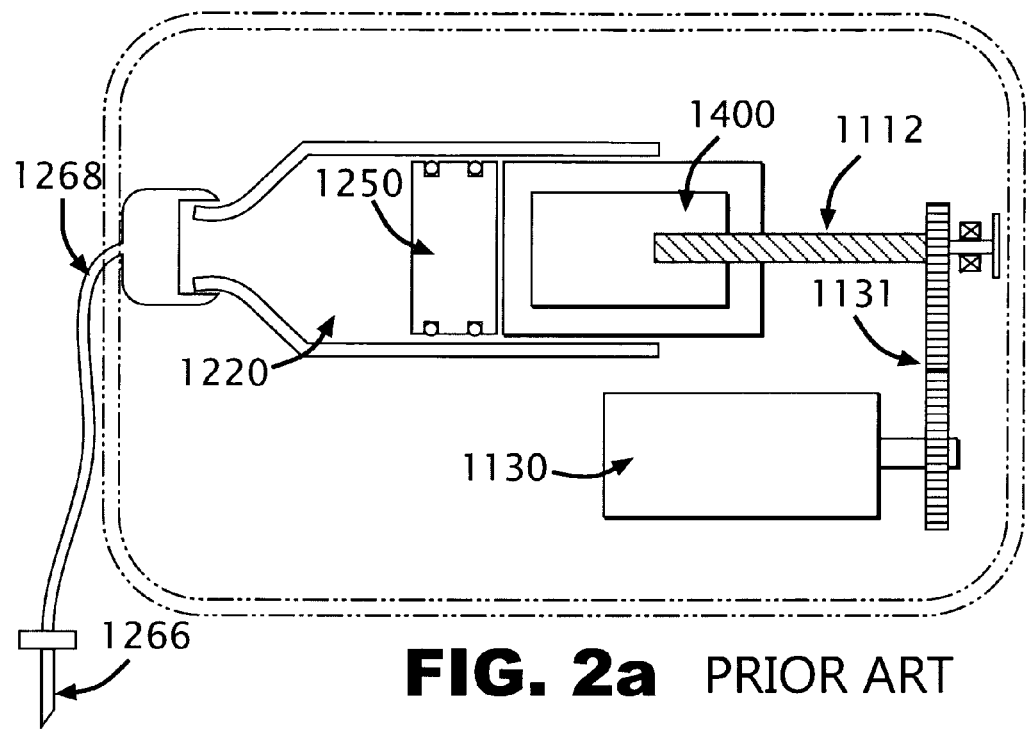
FIGS. 2*a*-2*f* show prior art driving mechanisms.
Figure 2B:
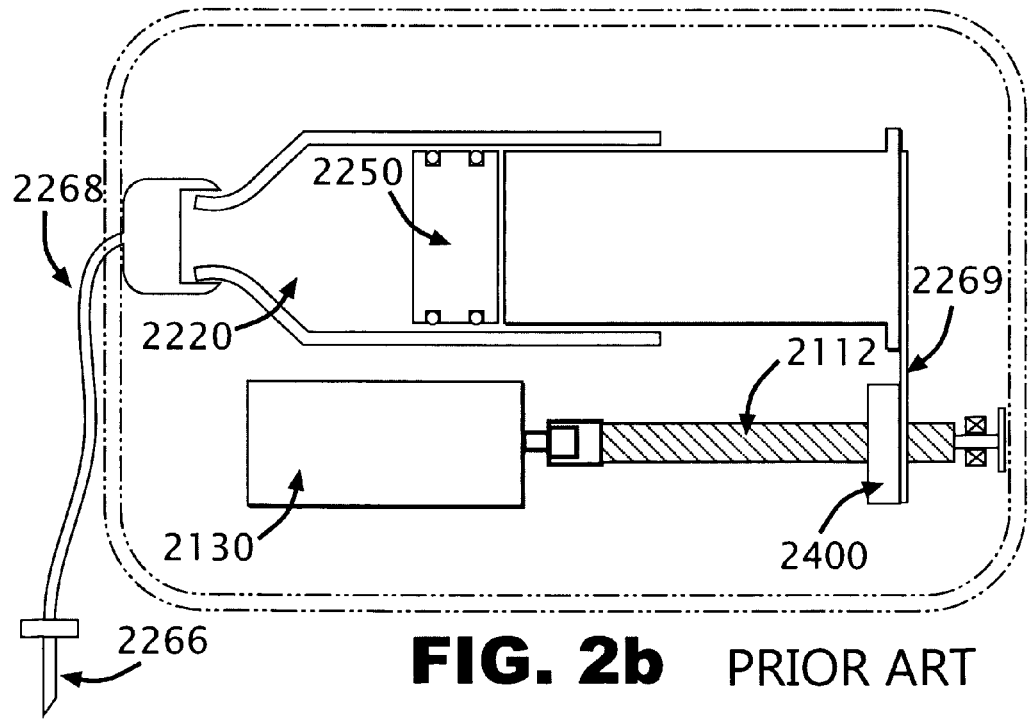
Figure 2C:
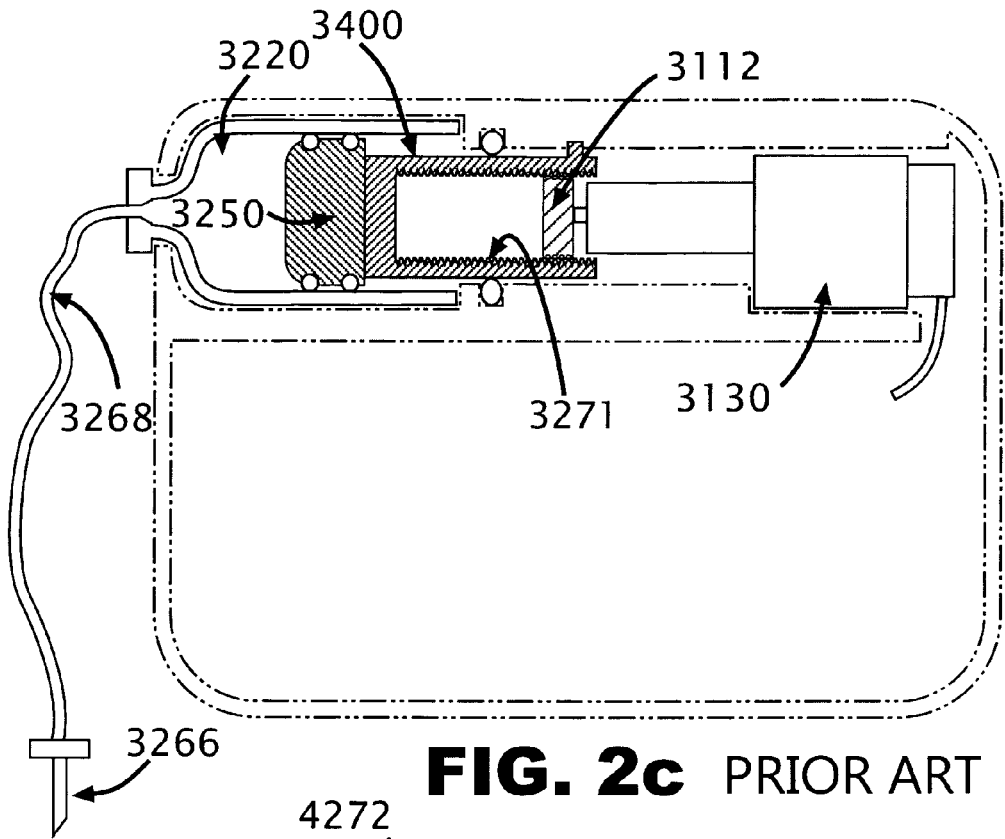
Figure 2D:
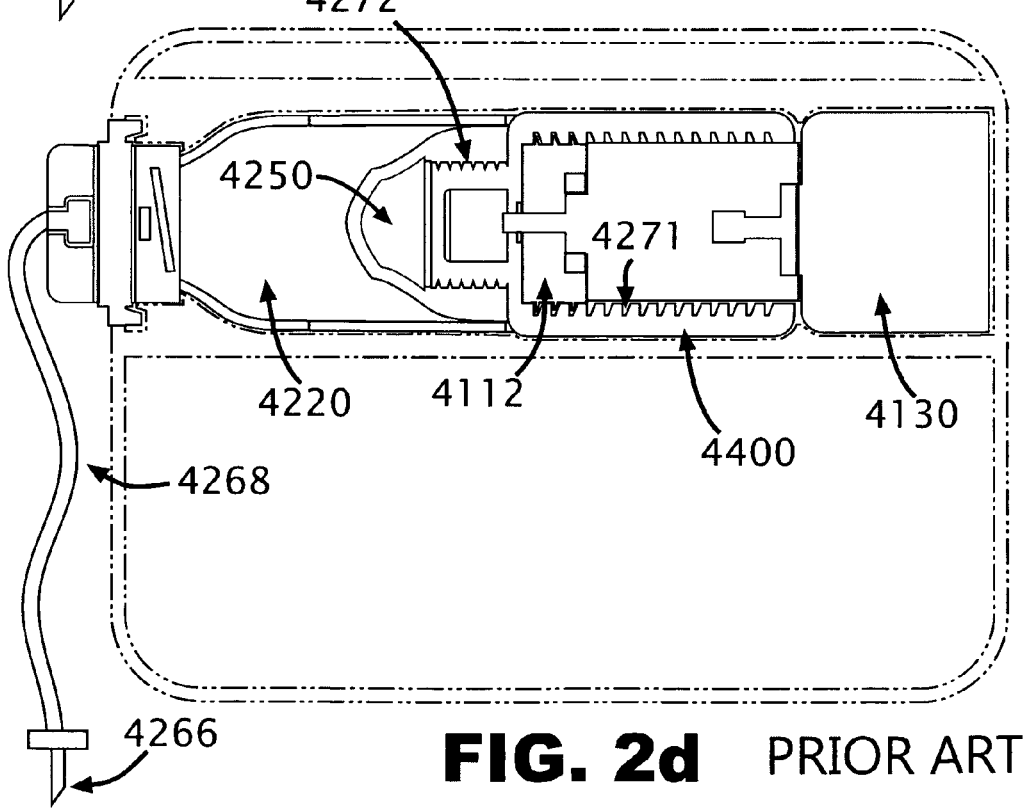
Figure 2E:
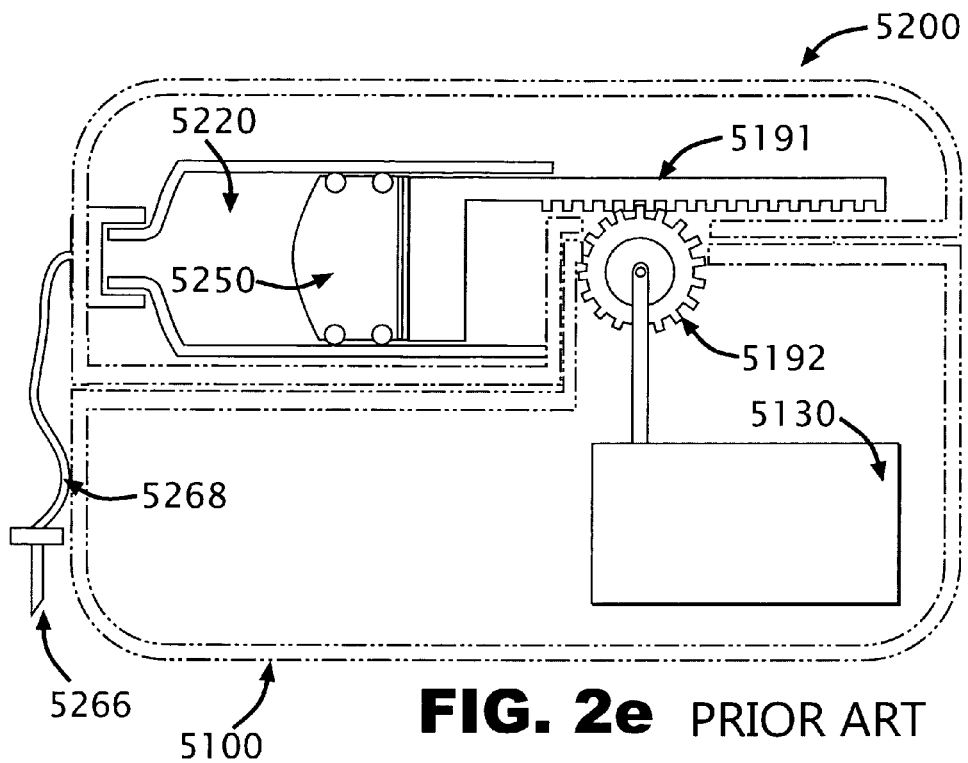
Figure 2F:
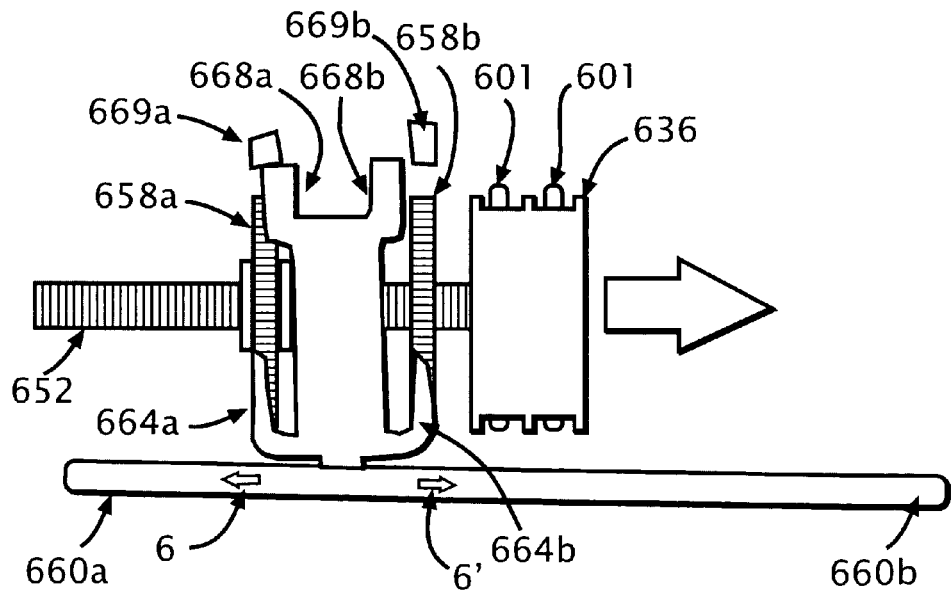

FIGS. 2a-2f show prior art driving mechanism configurations for piston-type pumps that comprise a plunger and a reservoir (e.g., a barrel). Specifically, FIGS. 2a-2d show configurations of "pager-like" pumps and FIGS. 2e-2f show configurations of skin-securable pumps. FIG. 2a illustrates a one-piece "pager-like" pump. Fluid (e.g., insulin) contained within a reservoir 1220 is delivered through a tube 1268 and transdermal cannula 1266 into the body of a patient. A motor 1130 rotates one or more gears 1131 that rotate a threaded drive screw 1112 (hereinafter "drive screw"). The drive screw 1112 rotates within a non-rotating nut 1400 to convert the rotational movement of the drive screw 1112 into linear displacement of the nut 1400 and forward movement of plunger 1250 within reservoir 1220.

FIG. 2b also illustrates a one-piece "pager-like" pump. Fluid (e.g., insulin) contained within a reservoir 2220 is delivered through a tube 2268 and a subcutaneously insertable cannula 2266 into the body of a patient. A motor 2130 rotates a drive screw 2112 that rotates within a non-rotating nut 2400. The non-rotation of nut 2400 causes the rotational movement of drive screw 2112 to be converted into linear movement to slide the nut 2400 over the drive screw 2112 to move a rigid bar 2269 that moves plunger 2250 within reservoir 2220.

FIG. 2c also illustrates a one-piece "pager-like" pump. Fluid (e.g., insulin) contained within a reservoir 3220 is delivered through a tube 3268 and a subcutaneously insertable cannula 3266 into the body of a patient. A motor 3130 rotates a drive screw 3112 within a non-rotating nut 3400 that contains inner threads 3271. The non-rotation of nut 3400 causes the rotational movement of drive screw 3112 to be converted into linear movement. As a result, the nut 3400 slides linearly and moves plunger 3250 within reservoir 3220.

FIG. 2d also illustrates a one-piece "pager-like" pump. Fluid (e.g., insulin) contained within a reservoir 4220 is delivered through a tube 4268 and a subcutaneously insertable cannula 4266 into the body of a patient. A motor 4130 rotates a drive screw 4112 within a non-rotating nut 4400 that contains inner threads 4271. The non-rotation of nut 4400 causes the rotational movement of drive screw 4112 to be converted into linear movement. As a result, the nut 4400 slides linearly and moves plunger 4250 within reservoir 4220. In this configuration, plunger 4250 may be preferably threaded onto an extension 4272 of the nut 4400 to avoid unintentional relative movement between plunger 4250 and nut 4400.

In the above-mentioned examples, a motor rotates a drive screw that is coupled to a non-rotating nut such that the rotation of the drive screw within the non-rotating nut causes the rotational movement of the drive screw to be converted into linear movement and displaces a plunger.

FIGS. 2e-2f show two examples of prior art driving mechanism configuration of a skin-securable pump. FIG. 2e illustrates a two-part skin-securable pump as described in U.S. Published Patent Application No. 2008/0097327 assigned to Medtronic MiniMed. In this pump, fluid contained within a reservoir 5220 is delivered through a tube 5268 and subcutaneously insertable cannula 5266 into the body of a patient. A disposable part 5200 contains a plunger 5250 rigidly connected to a threaded rod 5191. A motor 5130, contained within a reusable part 5100, rotates a drive wheel 5192. When the disposable part 5200 and reusable part 5100 are connected, the drive wheel 5192 linearly displaces the threaded rod 5191 and moves the plunger 5250 within reservoir 5220.

FIG. 2f illustrates a driving mechanism of a one-piece skin-adherable pump as described in U.S. Published Patent Application No. 2005/0238507 assigned to Insulet Corporation. In this pump, a plunger 636 comprises two gaskets 601 and is rigidly connected to a drive screw 652. Two cogwheels 658a, 658b are engaged with drive screw 652 and each contain skewed outer teeth. A left and right linear movement (indicated by arrows 6 and 6', respectively) of a Nitinol wire 660a, 660b tilts a fork with two lower arms 664a, 664b that slide over the skewed teeth and rotate cogwheels 658a, 658b. Two upper arms 668a, 668b of the fork are engaged at the end of the movement with connectors 669a, 669b for cycles counting.

Figure 3:
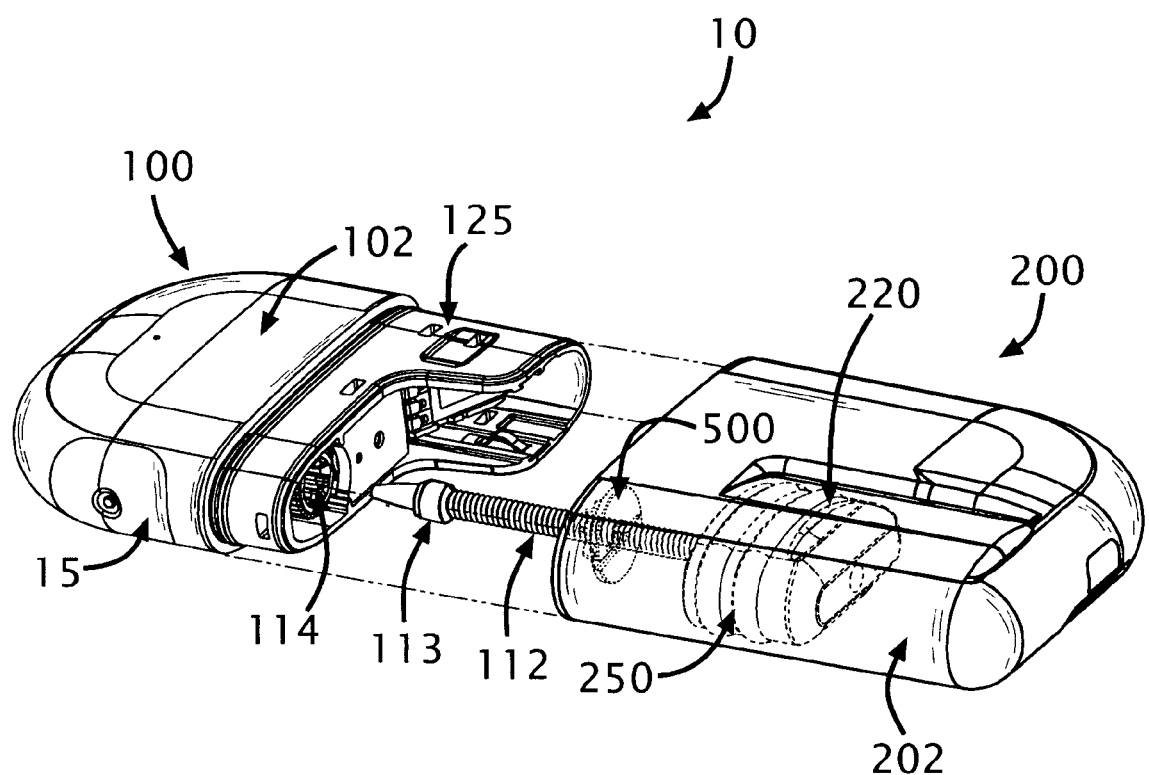
FIG. 3 shows a two-part fluid dispensing unit having a reusable part and a disposable part, according to some embodiments.
Figure 4A:
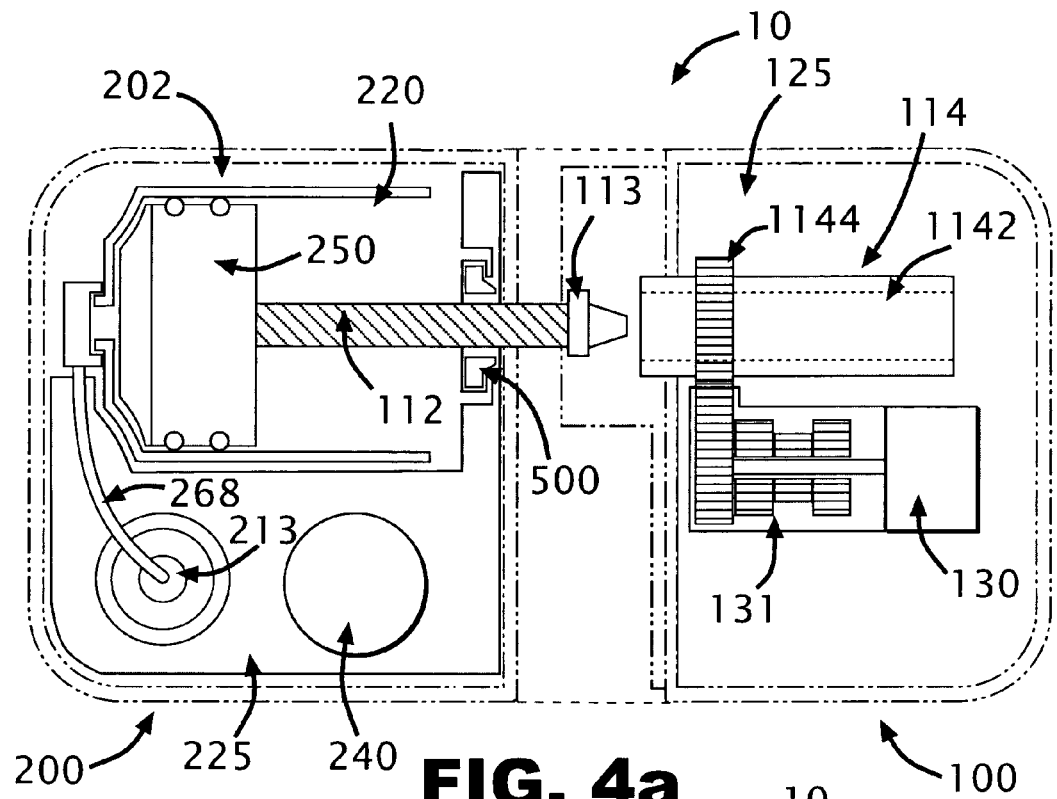
FIGS. 4*a*-4*b* show a two-part fluid dispensing unit before (FIG. 4*a*) and after (FIG. 4*b*) connection of the two parts of the unit, according to some embodiments.
Figure 4B:
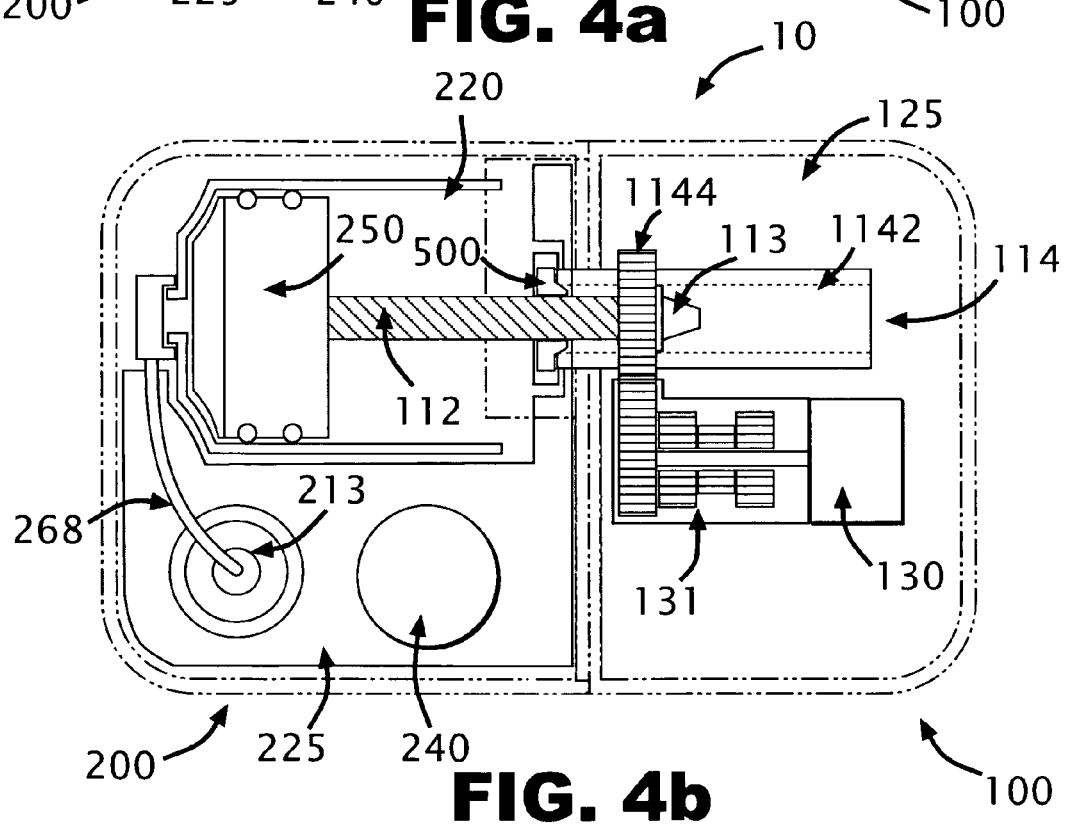

FIG. 3 shows an embodiment of a unit 10 according to the present disclosure that may be comprised of two parts, a reusable part 100 (hereinafter "RP") and a disposable part 200 (hereinafter "DP"). The RP 100 and the DP 200 may have housings (also referred to as "shells" or "pockets") 102 and 202, respectively, and chassis (also referred to as "inserts") 125 and 225, respectively (the DP chassis 225 is shown in FIGS. 4a-4b). The chassis 125 and 225 may serve as the internal structural framework of the RP 100 and DP 200, respectively, and may accommodate and/or provide attachment for any or all components within the housings 102, 202 of RP 100 and DP 200, respectively. The pumping mechanism of unit 10 may be a "piston-type" pump that includes a plunger 250 that may move within a reservoir 220 (e.g., a barrel type). In some embodiments, the RP 100 contains the relatively expensive components including without limitation the motor (not shown), the gears, including a rotating sleeve 114, electronics (not shown), and fluid dispensing buttons/switches 15 used for manually controlling and otherwise instructing at least the delivery of fluid without the aid of a remote control (see, e.g., RC 900 discussed above in FIG. 1). In some embodiments, the DP 200 contains the reservoir 220, the plunger 250 (in some embodiments, with gaskets), a drive screw 112 having a proximal end 113 (e.g., a conical tip) receivable within the rotating sleeve 114 (also referred to as "receiving portion" or "receiving component") and a distal end (not shown) connected to the plunger 250, and a drive nut 500 coupled to the drive screw 112. In some embodiments, the drive nut 500 may be contained within the RP 100, e.g., coupled to the rotating sleeve 114. In some embodiments, the drive screw 112 (also referred to as "plunger rod" or "threaded plunger rod") may be contained within the RP 100 and connectable to the plunger 250 of the DP 200 upon connection of the DP 200 with the RP 100. In some embodiments, one or more batteries (not shown) may also be included in the DP 200 and/or in the RP 100. Forward motion of the plunger 250 urges fluid from the reservoir 220. The cross-sectional shape of the reservoir 220 may be oval, elliptical and/or include a plurality of arches (e.g., four or eight arches) to maintain a low profile (e.g., thin shape) similar to a patch for fixation to the body of a patient. Examples of various reservoir cross-sectional shapes are disclosed in co-owned International Patent Application No. PCT/IL09/000641 (Publication No. WO2008/139458), filed May 11, 2008, claiming priority to U.S. Provisional Patent Application No. 60/928,815 and entitled "A Positive Displacement Pump," the content of all of which is hereby incorporated by reference in it entirety. In some embodiments, the housing 202 of the DP 200 may contain internal components and, in addition, serve as the walls of the reservoir 220 (i.e., a portion of the housing 202 may define the reservoir 220). The chassis 225 (not shown in FIG. 3) of the DP 200 may support a delivery tube 268 (not shown in FIG. 3), connecting lumen (not shown in FIG. 3) and/or one or more batteries (not shown in FIG. 3). The housing 102 of the RP 100 and/or the housing 202 of the DP 200 may also comprise a construction reinforcing means, as disclosed in co-owned International Patent Application No. PCT/IL09/000972, filed Oct. 11, 2009, claiming priority to U.S. Provisional Patent Application No. 61/103,383 and entitled "Dispensing Device with a Protective Shield," the content of which is hereby incorporated by reference in its entirety. In some embodiments, the drive screw 112 may be connected to the plunger 250. The proximal end 113 of the drive screw 112 may be any suitable shape, including without limitation, a conical shape or a hat shape. In some embodiments, when the RP 100 and the DP 200 are connected, the proximal end 113 of the drive screw 112 enters the rotating sleeve 114 of the RP 100 to guide the drive nut 500 into an engagement position with the rotating sleeve 114.

FIGS. 4a-4b show an embodiment comprising a two-part unit 10 before (FIG. 4a) and after (FIG. 4b) the RP 100 and DP 200 are connected. In some embodiments, the DP 200 may comprise a housing 202, a portion of which may also serve as walls of the reservoir 220, and a chassis 225. Embodiments of the DP 200 may include the reservoir 220, the slidable plunger 250 movable within the reservoir 220 and connected to a non-rotating drive screw 112, the drive nut 500, a delivery tube 268, an exit port 213 and an energy supply 240. In some embodiments, the energy supply 240 may be one or more batteries. In some embodiments, the energy supply 240 may be contained within the RP 100 and include one or more rechargeable batteries, as disclosed for example in co-owned International Patent Application No. PCT/IL09/000266, filed Mar. 10, 2009, claiming priority to U.S. Provisional Patent Application No. 61/035,288 and entitled "Infusion and Sensing Device with Battery Changing and Data Transferring Mechanisms," the content of all of which is hereby incorporated by reference in its entirety. In some embodiments, the drive nut 500 is captured within the chassis 225 so that it remains in place within the chassis 225 when the drive screw 112 moves forward or backward. In some embodiments, the RP 100 may include a motor 130, one or more gears 131, a rotating sleeve 114 and electronics (not shown). The rotating sleeve 114 may include an elongated portion 1142 capable of receiving the length of the drive screw 112 and a gear portion 1144 configured to interact with the motor 130 and/or the one or more gears 131.

When the RP 100 and the DP 200 are disconnected (FIG. 4a), an inner thread of the drive nut 500 is not engaged with the threads of the drive screw 112, whereby unit 10 is in a "disengaged position," according to some embodiments. When the RP 100 and DP 200 are connected (FIG. 4b), the proximal end 113 enters the rotating sleeve 114, and the drive nut 500 is placed within rotating sleeve 114, whereby unit 10 is an "engaged position," according to some embodiments. The engagement of the drive nut 500 with the rotating sleeve 114 forces threads 507 (see FIG. 5a) of the drive nut 500 to be engaged with external threads on the drive screw 112. Upon rotation of the rotating sleeve 114, the drive nut 500 also rotates. The non-rotation of the drive screw 112 causes the rotational movement of the drive nut 500 to be converted into linear movement and displaces the drive screw 112 and the plunger 250 within the reservoir 220.

Figure 5A:
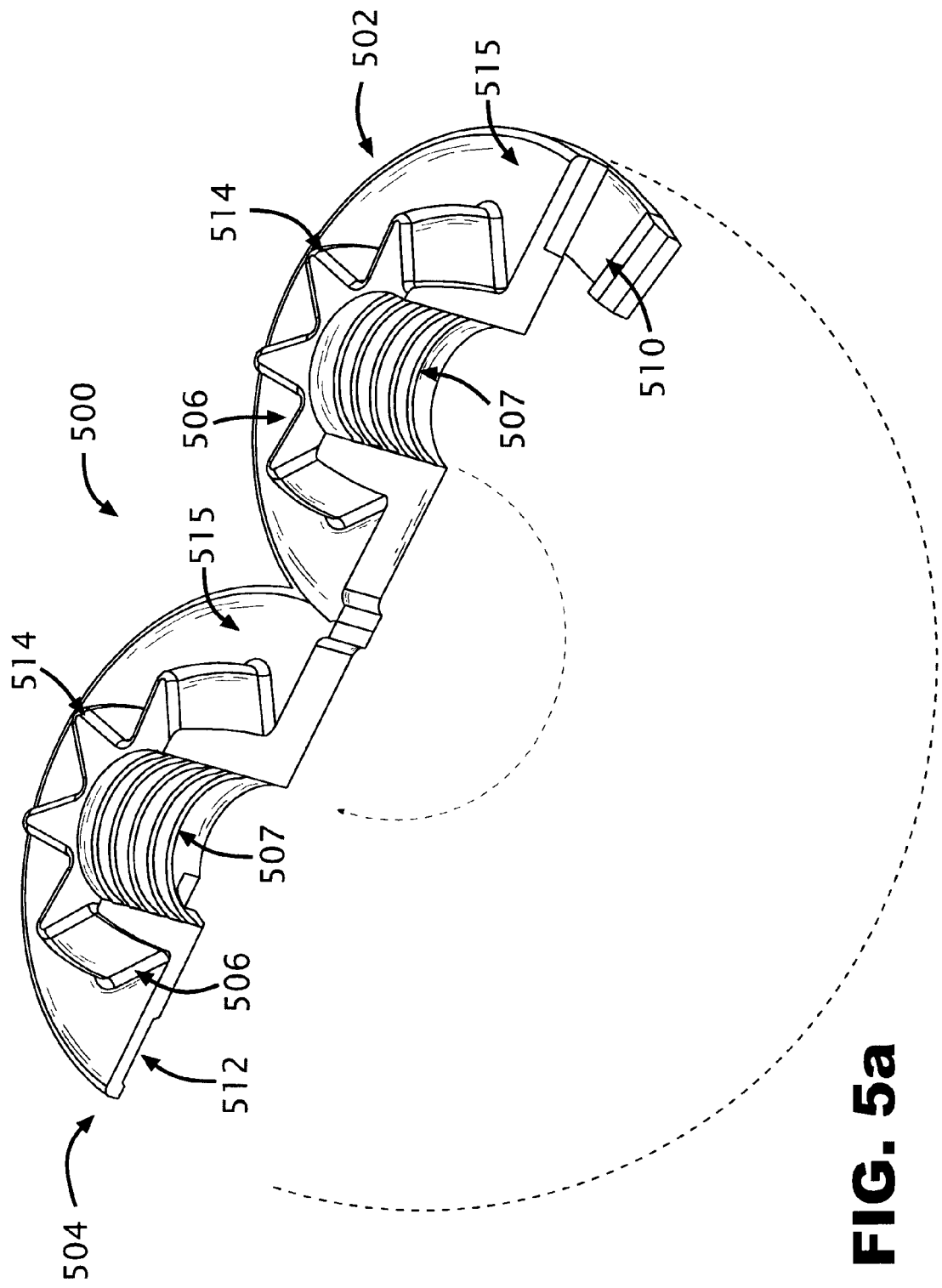
FIGS. 5*a*-5*c* show an embodiment of a drive nut in an open position (FIG. 5*a*) and a closed position (FIG. 5*b*-5*c*), before (FIG. 5*b*) and after (FIG. 5*c*) engagement of the drive nut with a rotating sleeve contained within the reusable part and a drive screw, according to some embodiments.
Figure 5B:
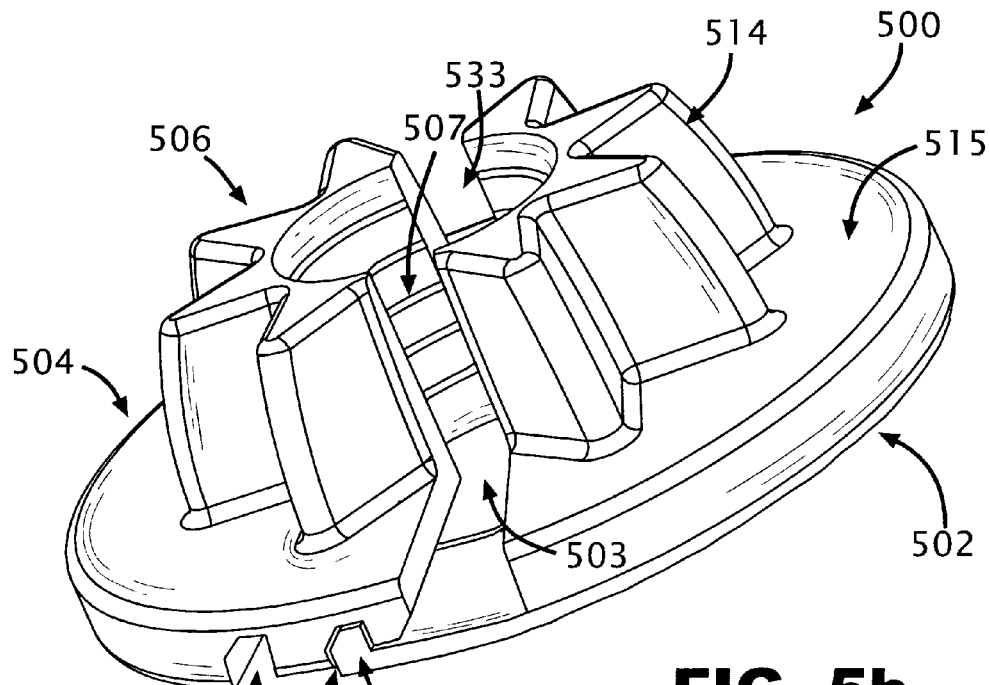
Figure 5C:
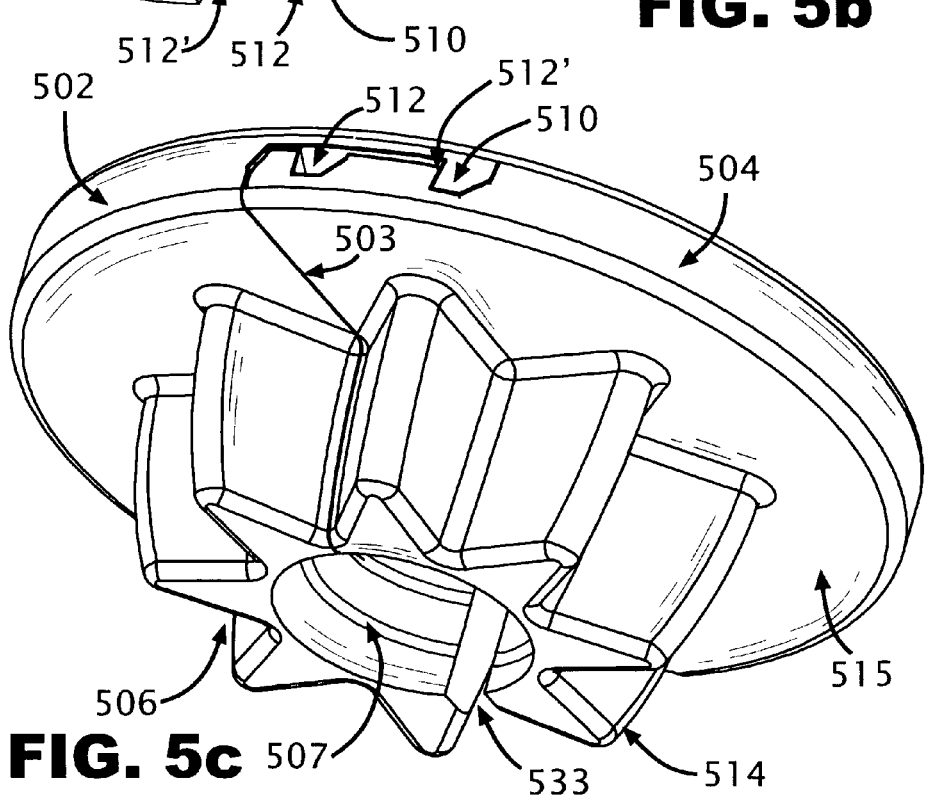
Figure 6A:
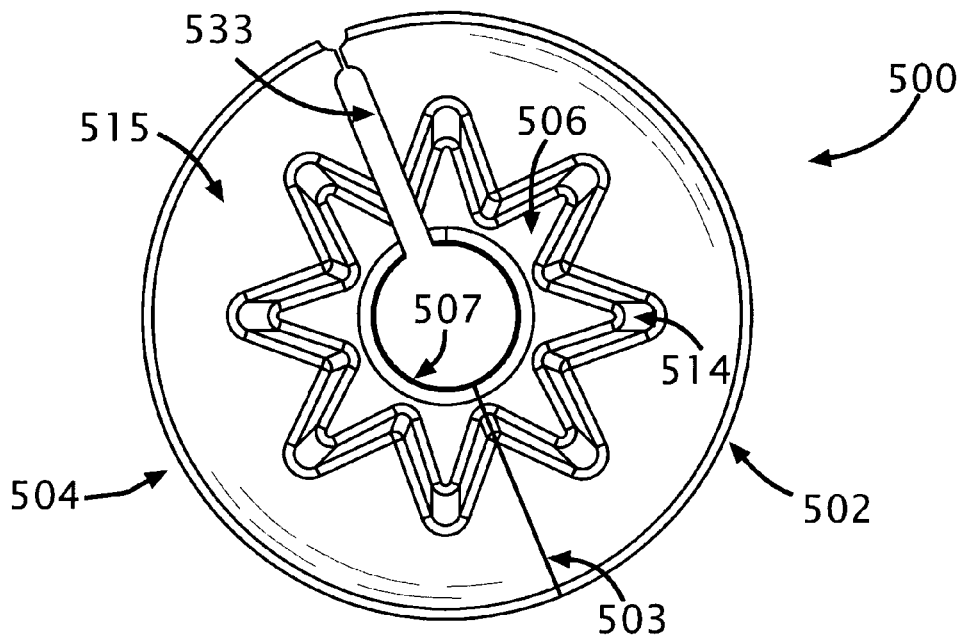
FIGS. 6*a*-6*b* show upper views of a drive nut (FIG. 6*a*) and a rotating sleeve (FIG. 6*b*), according to some embodiments.

FIGS. 5a-5c show various spatial views of the drive nut 500. In some embodiments, the drive nut 500 may be split (i.e., configured as a split-nut) to allow coupling of the drive nut 500 with the drive screw 112 during assembly and to support two operational modes: "disengaged" and "engaged." FIG. 5a shows the drive nut 500 in an open position before it is coupled with the drive screw 112. In some embodiments, the drive nut 500 may have two parts 502 and 504. In some embodiments, parts 502 and 504 may be connected in some manner, including without limitation, by a hinge. In some embodiments, parts 502 and 504 may be separate parts, detachably connectable to each other. Each part 502 and 504 may comprise a body portion 506 having internal threads 507 and external teeth 514, and a rounded plate 515, according to some embodiments. The external teeth 514 may be configured to form together a substantially conical shape and/or a curved shape (i.e., the longitudinal cross-section of the body portion 506 may be, for example, a truncated cone), according to some embodiments. Part 502 and/or part 504 may have at least one latch 510 for engaging parts 502 and 504 with each other. In some embodiments, as shown for example in FIG. 5a, the plate 515 of part 502 may have a latch 510 that connects it to the plate 515 of part 504. In some embodiments, the latch 510 secures parts 502 and 504 by engaging with one or more grooves 512 formed in part 504, for example (see FIG. 5b). FIG. 5b shows a spatial view of the drive nut 500 in a closed, disengaged position, wherein the latch 510 is engaged with groove 512. In some embodiments, one or more slits 503, 533 are formed between parts 502 and 504, as best shown in FIG. 6a. In the disengaged position, the one or more slits 503, 533 are said to be "open," whereby one or more gaps exist between the body portion 506 (i.e., the threads 507 and teeth 514) of part 502 and the body portion 506 (i.e., the threads 507 and teeth 514) of part 504 such that the drive screw 112 is not engaged with threads 507 and can freely slide back and forth within the drive nut 500. In some embodiments, one or more additional slits (not shown) may be formed in part 502 and/or in part 504. FIG. 5c shows a spatial view of the drive nut 500 in a closed, engaged position. In some embodiments of this position, the latch 510 may be engaged with groove 512'. As a result, the one or more slits 503, 533 are narrowed. According to some embodiments, in the engaged position, at least one slit, e.g., slit 503, is said to be "closed," thereby eliminating the corresponding gap between the body portion 506 of part 502 and the body portion 506 of part 504, whereas at least one other slit, e.g., slit 533, although narrowed remains "open," thereby maintaining a corresponding gap between the body portion 506 of part 502 and the body portion 506 of part 504, to provide the drive nut 500 with elasticity when in the engaged position. In some embodiments of this engaged position the threads of drive screw 112 engage with the internal threads 507 of the drive nut 500. Because the drive screw 112 is fixed in a non-rotating configuration, the rotational movement of drive nut 500 about the drive screw 112 is converted into linear movement and displaces the drive screw 112 and plunger 250 within reservoir 220.

Figure 6B:
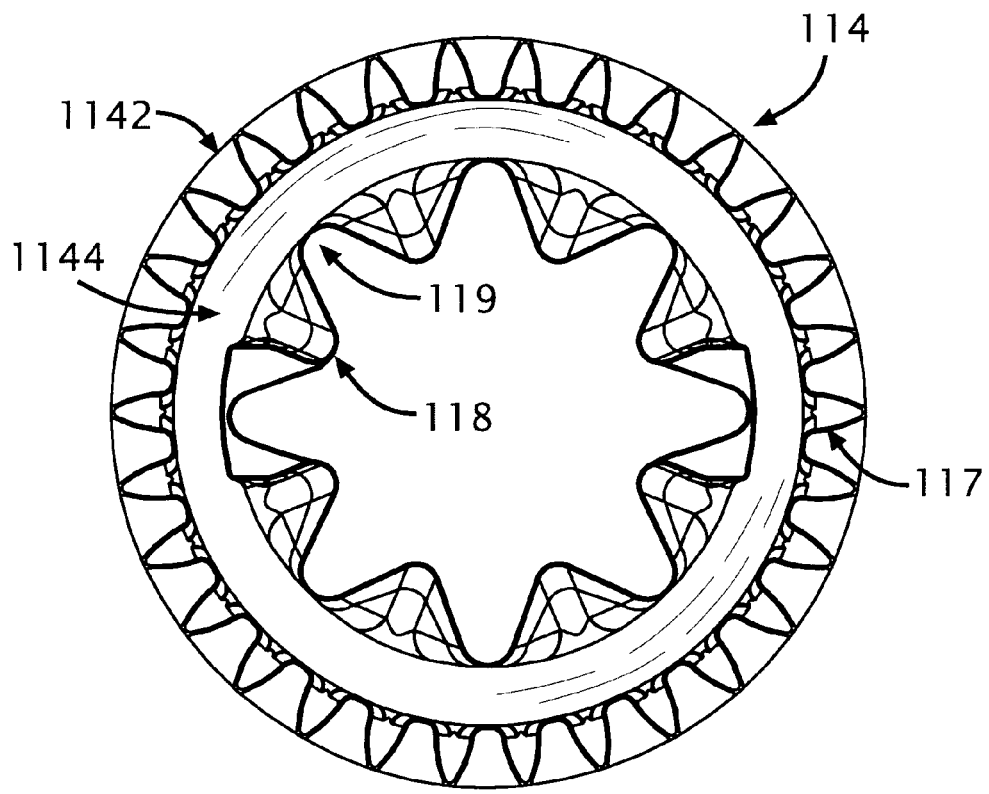

FIGS. 6a-6b show upper views of the drive nut 500 (FIG. 6a) and the rotating sleeve 114 (FIG. 6b). In some embodiments, the drive nut 500 may comprise two parts 502 and 504, each having a rounded plate 515 and a body portion 506 with internal threads 507 and external teeth 514. In some embodiments, the rotating sleeve 114 may comprise inner teeth 118 and outer teeth 117. The inner teeth 118 and the outer teeth 117 may be provided on the gear portion 1144 of the rotating sleeve 114. In some embodiments, at least a portion of the elongated portion 1142 may also comprise inner teeth 118, e.g., the inner teeth 118 may extend along the entire length of the rotating sleeve 114, including both the gear portion 1144 and the elongated portion 1142. The inner teeth 118 may define inner grooves 119. In some embodiments, the inner grooves 119 may have a shape and/or dimensions substantially matching the shape and/or dimensions of the external teeth 514 of the drive nut 500. In some embodiments, the outer teeth 117 of the rotating sleeve 114 may be configured as gear teeth adapted to mesh with teeth of one or more gears (not shown) of the RP 100. Before engagement of the drive nut 500 with the rotating sleeve 114, parts 502 and 504 of the drive nut 500 may be in the disengaged position, whereby the one or more slits 503, 533 are open, i.e., one or more gaps exist between the threads 507 and teeth 514 of part 502 and threads 507 and teeth 514 of part 504 such that the threads of the drive screw 112 are not engaged with the threads 507 of the drive nut 500 and the drive screw 112 can freely slide back and forth within the drive nut 500. To provide an engaged position as shown in FIG. 6a, parts 502 and 504 are brought together (see FIGS. 5a-5c). As stated above, in some embodiments, at least one of the slits, e.g., slit 533, remains open in the engaged position, although narrowed relative to its state when the drive nut 500 is in the disengaged position, to provide elasticity to the drive nut 500 and thus eliminate and/or minimize the risk of undesired deformities due to applied stresses. In this position, the drive nut 500 may engage with the rotating sleeve 114 by having the teeth 514 of the drive nut 500 mesh with the inner teeth 118 of the rotating sleeve 114. Also in this position, the threads 507 of the drive nut 500 may engage the threads of the drive screw 112. Accordingly, rotation of the rotating sleeve 114 will result in rotation of the drive nut 500 due to the engagement between teeth 514 and inner teeth 118. Moreover, because the drive screw 112 does not rotate, the rotational movement of the drive nut 500 about the drive screw 112 will be converted into linear movement and displace the drive screw 112 (and plunger 250 connected thereto) within reservoir 220. It should be borne in mind that any other engagement and/or locking mechanisms known to those skilled in the mechanical arts may also be provided for engaging the drive nut 500 with the rotating sleeve 114 and/or for engaging the drive nut 500 with the drive screw 112. For example, flexible nut teeth that can be squeezed towards the drive screw 112 upon engagement of the drive nut 500 and rotating sleeve 114 may be employed, as well as any other force-induced locking mechanism.

Figures 7A, 7B:
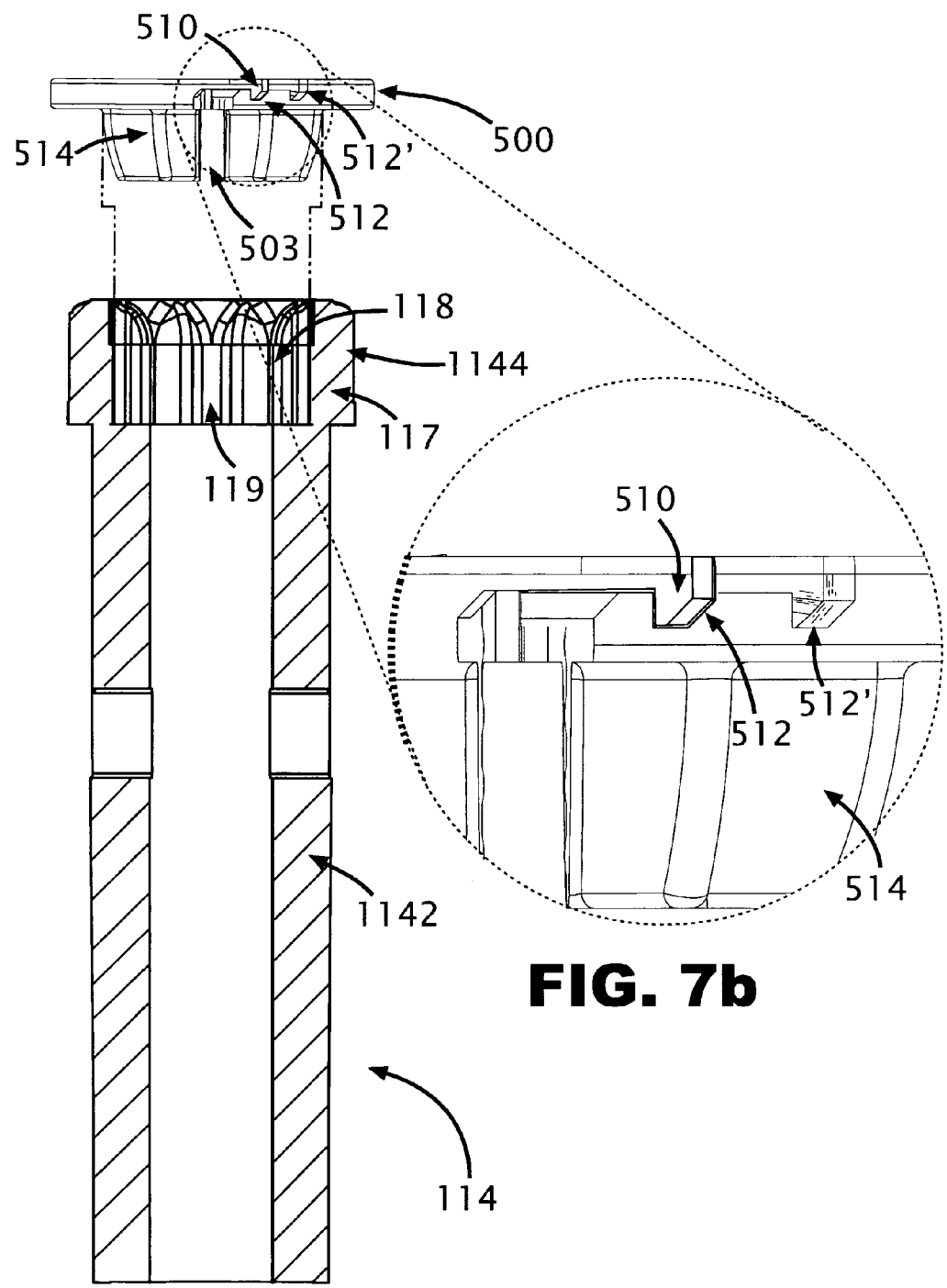
FIGS. 7*a*-7*c* show longitudinal cross-sectional views of a drive nut before (FIGS. 7*a*-7*b*) and after engagement with a rotating sleeve (FIG. 7*c*), according to some embodiments.
Figure 7C:
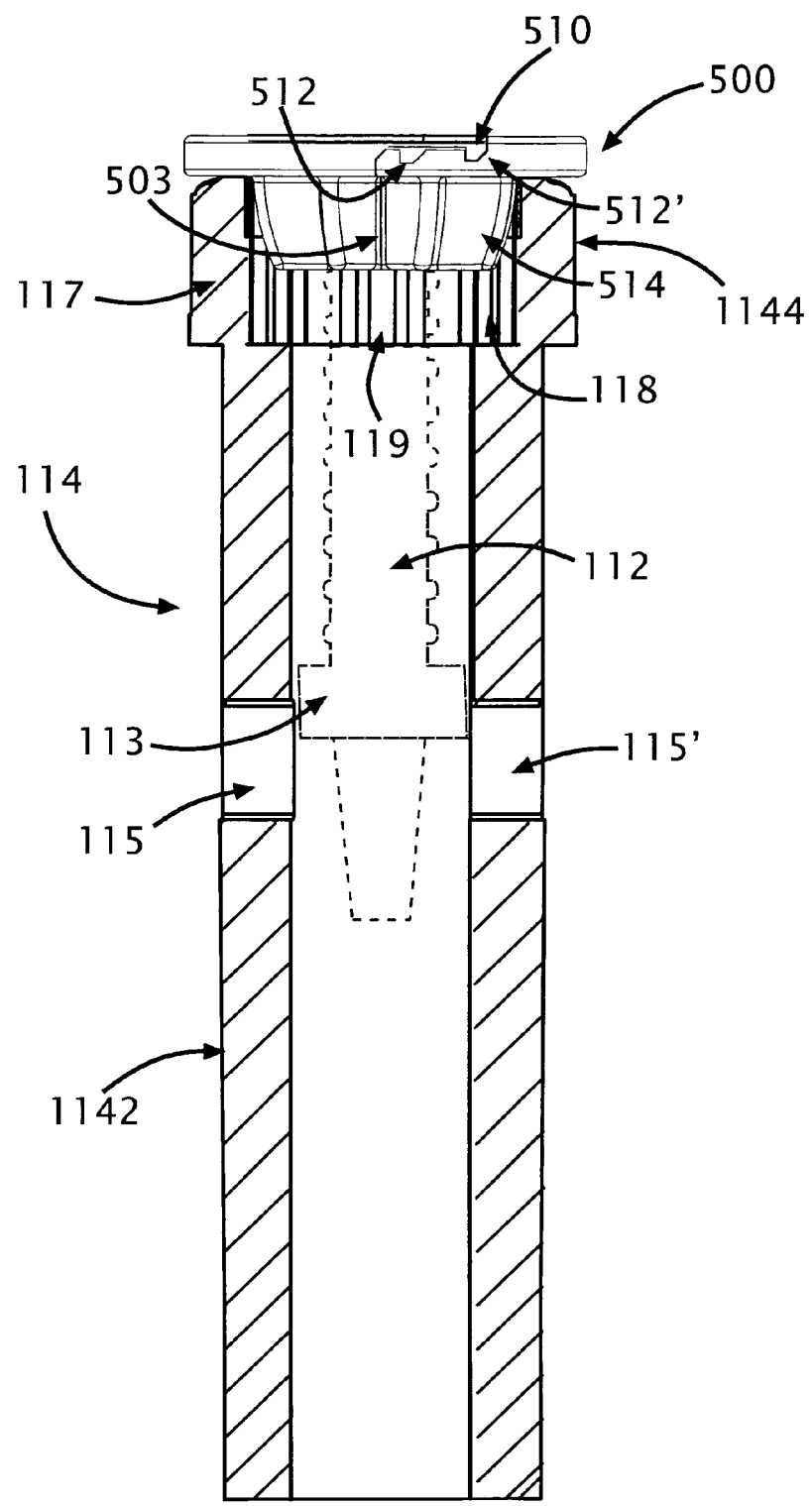

FIGS. 7a-7c show a longitudinal cross-sectional view of the drive nut 500 before (FIGS. 7a-7b) and after (FIG. 7c) engagement with the rotating sleeve 114. As shown in FIGS. 7a-7b, before engagement with the rotating sleeve 114, the drive nut 500 may be locked in a disengaged position by latch 510, according to some embodiments. Furthermore, in some embodiments of the disengaged position, it may have latch 510 engaged with groove 512 so as to maintain the slit 503 open. The rotating sleeve 114 may comprise inner teeth 118, defining inner grooves 119, and outer teeth 117 for interacting with teeth of one or more gears (not shown) that rotate the rotating sleeve 114. As shown in FIG. 7c, when the drive nut 500 is in the engaged position, the drive nut 500 may engage with the rotating sleeve 114, according to some embodiments. Upon engagement of the drive nut 500 with the rotating sleeve 114, the teeth 514 of the drive nut 500 may engage with the inner teeth 118 of the rotating sleeve 114 (i.e., the teeth 514 may be received by the grooves 119 defined by the inner teeth 118), and the latch 510 may engage with groove 512'. In this position, rotation of the rotating sleeve 114 by one or more gears 131 (not shown in FIG. 7c), or directly by the motor 130 (not shown in FIG. 7c), also rotates the drive nut 500. In some embodiments, the drive nut 500 may be capable of returning to the disengaged position upon disengagement from the rotating sleeve 114. In some embodiments, upon disengagement of the drive nut 500 from the rotating sleeve 114, the latch 510 may be released from the groove 512', either automatically or manually, resulting in the disengagement of the threads 507 (not shown in FIG. 7c) of the drive nut 500 from the threads of the drive screw 112.

In some embodiments, the rotating sleeve 114 does not comprise the elongated portion 1142, i.e., the rotating sleeve 114 may be configured as a gear (or cogwheel) having inner teeth 118 and outer teeth 117. In the engaged position of this embodiment, the drive screw 112 may protrude through the rotating sleeve 114 without being concealed within the rotating sleeve 114.

In some embodiments, the proximal end 113 of the drive screw 112 may serve as a position detector to monitor the position of the drive screw 112 within the rotating sleeve 114. Because the relative movement of the drive screw 112 with respect to the rotating sleeve 114 correlates to the position of the plunger 250 within the reservoir 220, the position of the drive screw 112 within the rotating sleeve 114 may be used as an indicator for fluid volume residing in the reservoir 220. In some embodiments, at least one set of windows, e.g., windows 115 and 115', may be formed in the elongated portion 1142 of the rotating sleeve 114 to operate in conjunction with at least one pair of an energy (e.g., light) source and energy (e.g., light) detector (not shown) to monitor relative movement between the drive screw 112 and the rotating sleeve 114, as disclosed, for example, in co-owned International Patent Application No. PCT/IL09/000388 (Publication No. WO2009/125398), filed Apr. 7, 2009, claiming priority to U.S. Provisional Patent Application No. 61/123,509 and entitled "Systems, Devices and Methods for Fluid Delivery," the content of all of which is hereby incorporated by reference in its entirety. In some embodiments, the energy source and energy detector may be positioned opposite each other and on opposite sides of the elongated portion 1142 of the rotating sleeve 114, such that when the energy source and the energy detector are aligned with the windows 115 and 115', e.g., every one half of a turn of the rotating sleeve 114, energy emitted by the energy source passes through the windows 115 and 115' and is received by the energy detector, unless the space between window 115 and window 115' is occupied by the drive screw 112 and/or its tip 113, which block the energy. Thus, in some embodiments, the amount of energy (e.g., light) detected by the energy detector is indicative of the fluid level inside the reservoir.

FIGS. 8a-8b show a filling process of the reservoir 220 of DP 200. In some embodiments, a filling adapter 62 may be used to couple a vial 60 with the exit port 213 (see FIGS. 4a-4b) of DP 200, as disclosed, for example, in co-owned International Patent Application No. PCT/IL09/000388 (Publication No. WO2009/125398). The filling adapter 62 may comprise a first end capable of being coupled to the exit port 213 and a second end capable of being coupled to the vial 60 to allow fluid communication between the vial 60 and the exit port 213, and thus between the vial 60 and the reservoir 220. A push-pull rod 70 may be removably connected to the drive screw 112. The push-pull rod 70 may serve as an auxiliary handle for more convenient gripping of the drive screw 112 by the user, and may be referred to as a "handle" or "auxiliary handle." During the filling process, the drive nut 500 is in a disengaged position, according to some embodiments. In this position, the drive screw 112 can freely slide back and forth within the drive nut 500. During the filling process, a user may pull the push-pull rod 70 and drive screw 112 backward (indicated by an arrow in FIG. 8a) until drawing from the vial 60 a desired volume of fluid into the reservoir 220. Any desired volume between zero and full capacity of the reservoir 220 (e.g., 2 cc) can be achieved. To eliminate the presence of any air bubbles appearing in the fluid, a user can repeatedly push and pull the push-pull rod 70 until the air is removed from the reservoir 220 and the desired volume is achieved. During the filling process of the reservoir 220, the drive nut 500 may be secured within the chassis 225 of the DP 200 and thus cannot move as the drive screw 112 moves. After filling the reservoir 220, the vial 60 is removed and the adapter 62 and push-pull rod 70 may be removed from the DP 200. In some embodiments, to allow refilling of the reservoir 220, the drive nut 500 is capable of returning to the disengaged position upon disengagement from the rotating sleeve 114, e.g., by releasing the latch 510 from the groove 512', either manually or automatically. As a result, the threads of the drive screw 112 disengage from the threads 507 of the drive nut 500, and the drive screw 112 can freely slide back and forth within the drive nut 500.

Figures 9A, 9B:
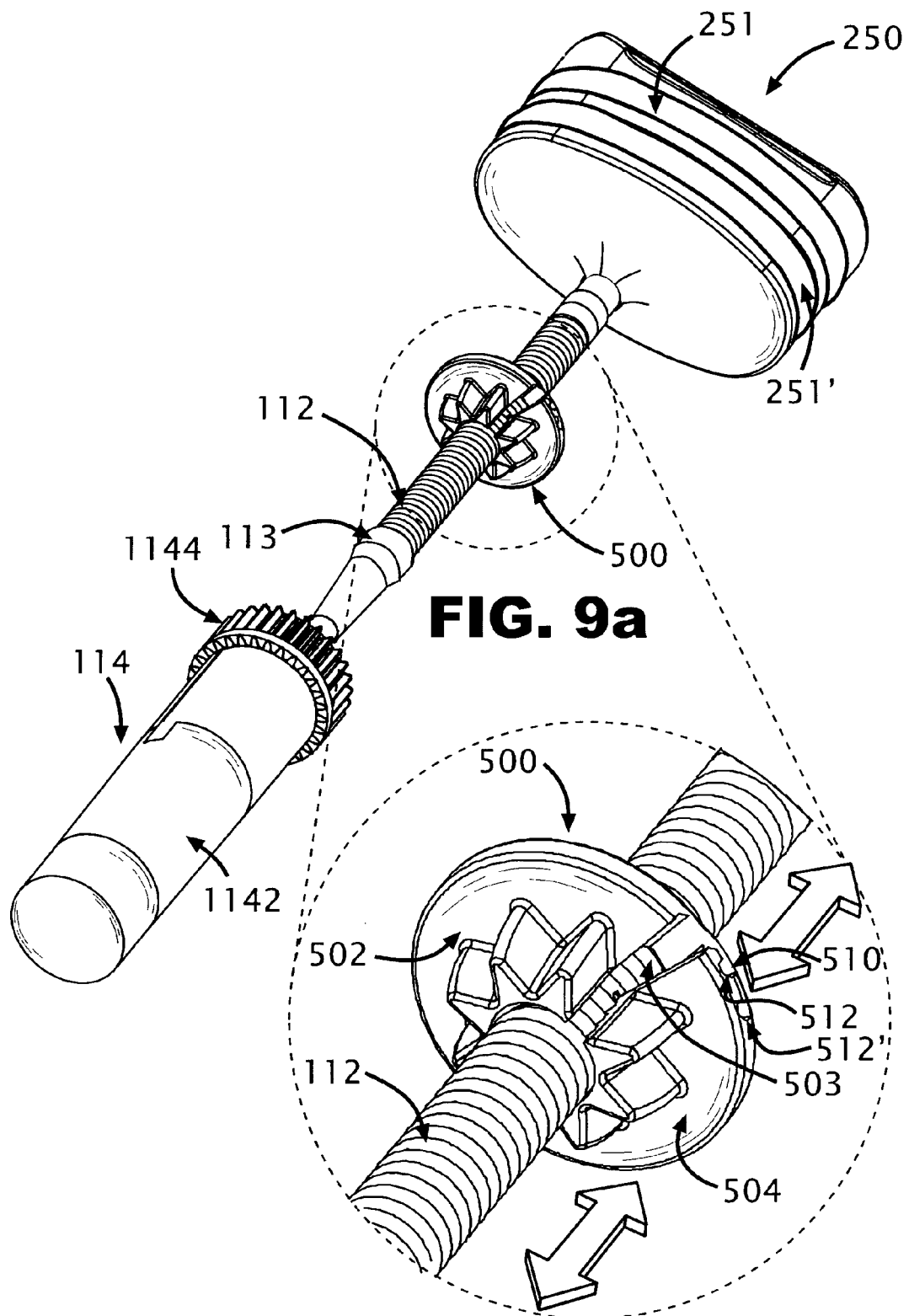
FIGS. 9a-9b show a drive screw coupled with a drive nut before engagement with a rotating sleeve, according to some embodiments.

FIGS. 9a-9b show the plunger 250 and drive nut 500 contained within the DP 200 before engagement with the rotating sleeve 114 contained within the RP 100. In some embodiments, the plunger 250 may be provided with one or more gaskets 251 and 251'. The plunger 250 may be rigidly coupled to the drive screw 112. In some embodiments, the plunger 250 may be unitary with the drive screw 112, so as to form together an integral member. The proximal end 113 of the drive screw 112 may be shaped to facilitate smooth, aligned engagement with the rotating sleeve 114. Such shapes may include without limitation a cone shape or hat shape. As shown in FIG. 9b, the drive nut 500 may be coupled to the drive screw 112. FIG. 9b further shows the drive nut 500 in a disengaged position, whereby the latch 510 is engaged with the groove 512, parts 502 and 504 are connected and slit 503 is open, such that a gap exists between the threads 507 and teeth 514 of part 502 and the threads 507 and teeth 514 of part 504 and the drive screw 112 is thus not engaged with the threads 507 and can freely slide back and forth within the drive nut 500 (as indicated by the double-headed arrows in FIG. 9b).

FIGS. 10a-10b show the drive nut 500 within the rotating sleeve 114 before final engagement, according to some embodiments. Here, the drive screw 112 resides partially within the rotating sleeve 114, the drive nut 500 is in the disengaged position and latch 510 is engaged with groove 512. In some embodiments, the drive nut 500 should be in the engaged position in order for the external teeth 514 of the drive nut 500 to properly mesh with the inner teeth 118 (not shown in FIGS. 10a-10b) of the rotating sleeve 114 (i.e., to be aligned with the inner grooves 119 (not shown in FIGS. 10a-10b)). Therefore, in some embodiments, during the final stage of engagement, the rotating sleeve 114 forces the drive nut 500 into the engaged position, i.e., the inner teeth 118 of the rotating sleeve 114 forcibly squeeze together the teeth 514 of parts 502 and 504 of the drive nut 500, until latch 510 disengages from groove 512 and engages with groove 512', thus narrowing the slit 503 (see FIGS. 7a-7c). In some embodiments, the latch 510 may be flexible, at least in part, to enable disengagement of the latch 510 from groove 512 and subsequent engagement of the latch 510 with groove 512'.

Figure 11:
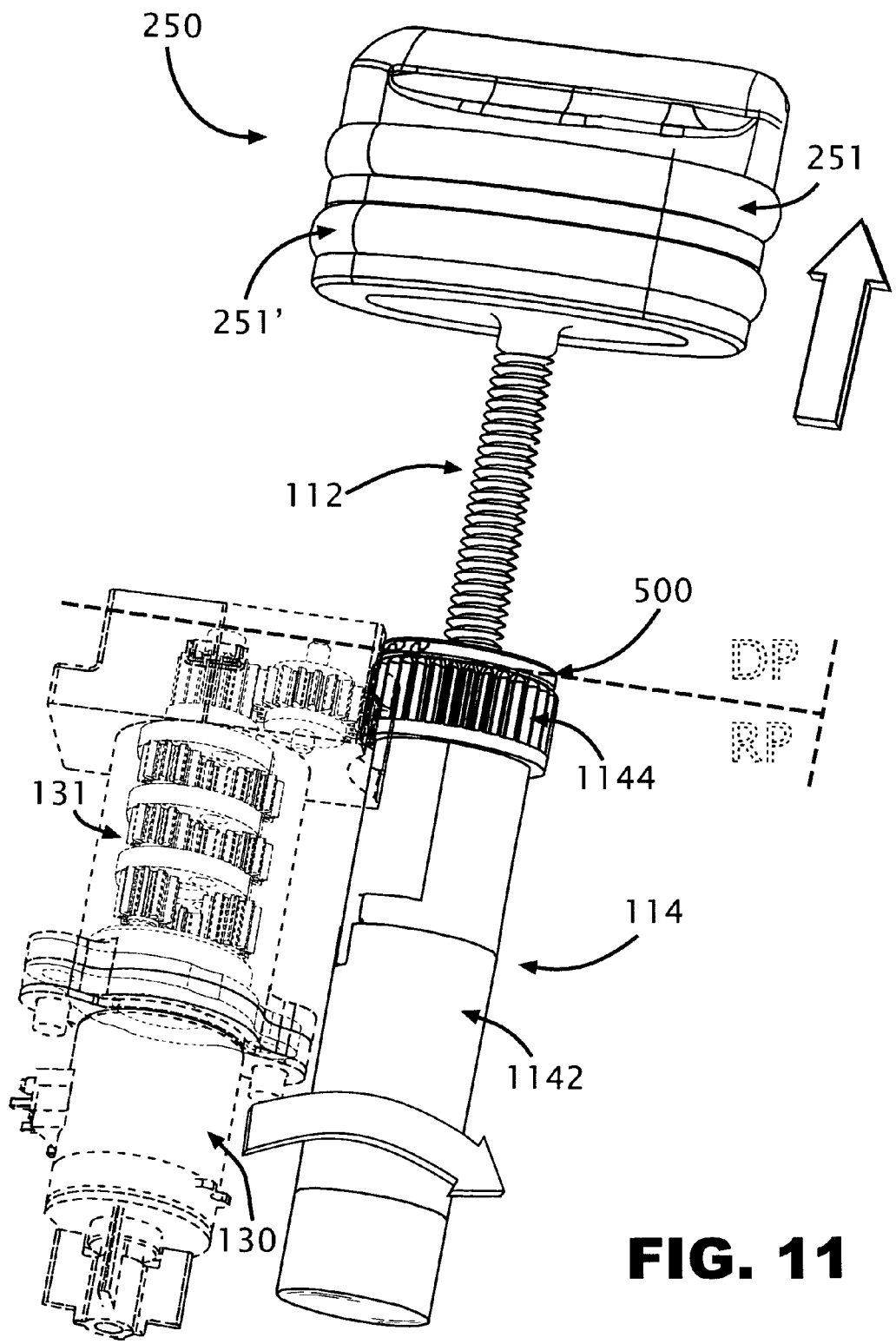
FIG. 11 shows internal components of a two-part skin-securable fluid dispensing unit where components within the two parts are connected together, according to some embodiments.

FIG. 11 shows the driving mechanism of a two-part infusion pump having a DP 200 and an RP 100, according to some embodiments. In some embodiments, the plunger 250, drive screw 112, and drive nut 500 may be contained within the DP 200 and the motor 130, one or more gears 131 and rotating sleeve 114 may be contained within the RP 100. FIG. 11 shows the drive nut 500 engaged with the rotating sleeve 114. In this position, the motor 130 may rotate the one or more gears 131 (including planetary gear) and rotating sleeve 114. The rotation of the rotating sleeve 114 (indicated by the curved arrow) rotates the drive nut 500. Because the drive screw 112 is fixed in a non-rotating configuration, the rotational movement of the drive nut 500 about the drive screw 112 is converted into linear movement and displaces the drive screw 112 (and plunger 250 connected thereto) within reservoir 220 (indicated by the straight arrow). Forward movement of the plunger 250 within the reservoir 220 dispenses fluid from the reservoir 220 to the exit port 213 (see FIGS. 4a-4b), in some embodiments through the delivery tube 268 (see FIGS. 4a-4b). In some embodiments, the drive nut 500 may be contained within the RP 100, e.g., the drive nut 500 may be coupled to the rotating sleeve 114 such that the final stage of engagement, as described above with regard to FIGS. 10a-10b, occurs upon insertion of the drive screw 112 of the DP 200 into the rotating sleeve 114 of the RP 100 through the drive nut 500.

Figure 12:
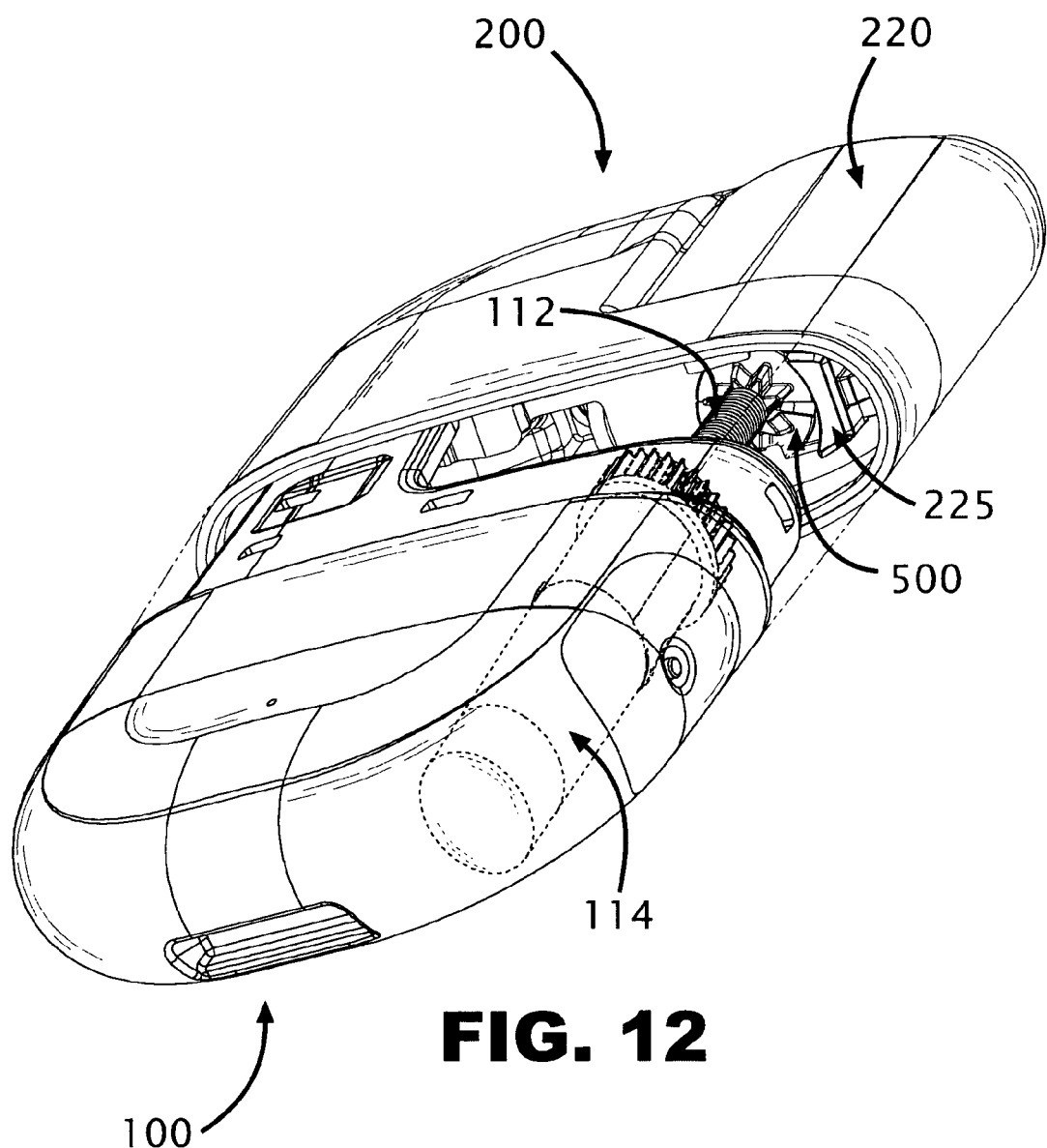
FIG. 12 shows a two-part skin-securable fluid dispensing unit before connection, according to some embodiments.

FIG. 12 shows the assembly of a two-part unit 10, according to some embodiments. Here, the RP 100 may contain the rotating sleeve 114 and the DP 200 may contain the reservoir 220. The drive nut 500 may be secured within the chassis 225 of the DP 200 and the drive screw 112 may be aligned with the rotating sleeve 114.

Figure 13A:
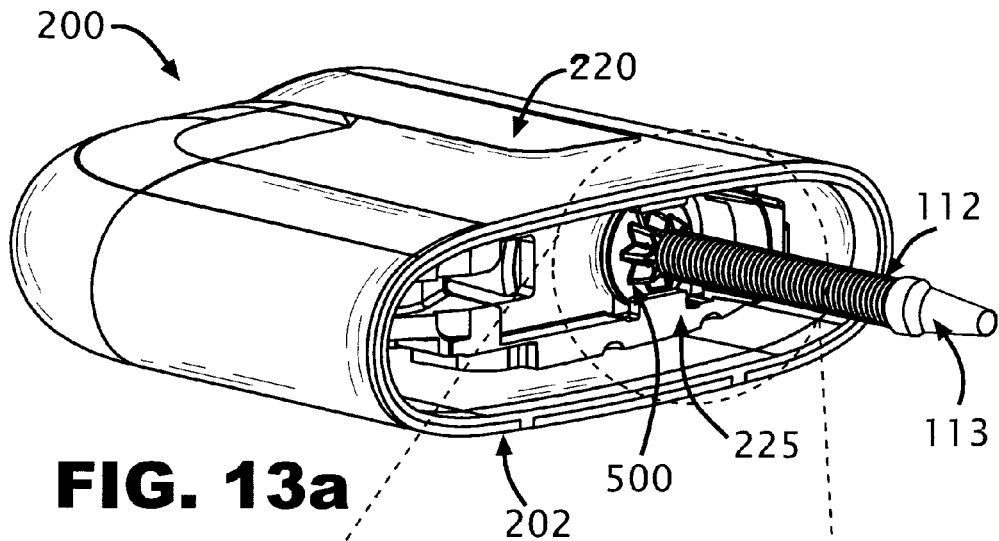
FIGS. 13a-13b show a configuration of a drive screw and a drive nut contained within a disposable part of the device, according to some embodiments.
Figure 13B:
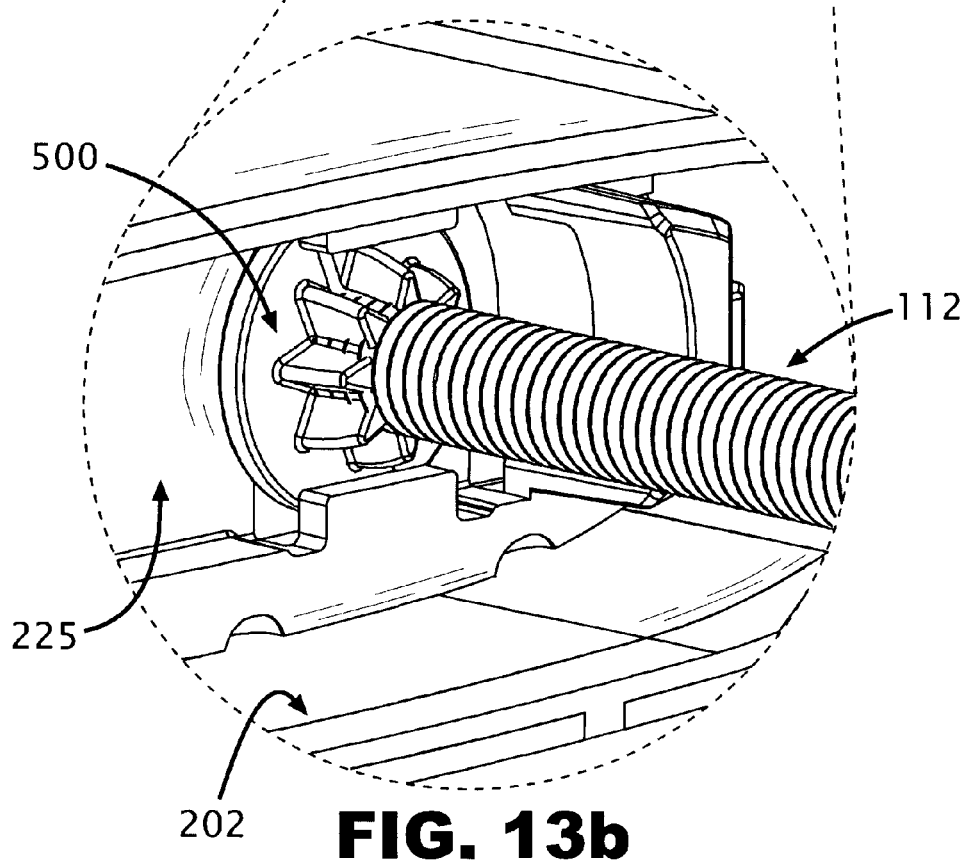

FIGS. 13a-13b show a DP 200 having a housing 202 and a chassis 225. A portion of the housing 202 may serve also as the walls of the reservoir 220 (i.e., a portion of the housing 202 of the DP 200 may define the reservoir 220). The drive screw 112 may be located in the DP 200 and have a proximal end 113 (e.g., configured as a conical tip). The drive nut 500 may be secured within the chassis 225 of the DP 200.

Any and all references to publications or other documents, including but not limited to, patents, patent applications, articles, webpages, books, etc., presented in the present application, are herein incorporated by reference in their entirety.

Although particular embodiments have been disclosed herein in detail, this has been done by way of example for purposes of illustration only and is not intended to be limiting with respect to the scope of the appended claims. Other embodiments, advantages and modifications are considered to be within the scope of the claims.

What is claimed is:
1. A method for delivering fluid, the method comprising:
providing a fluid delivery device having a reusable part that includes a motor and one or more gears and a disposable part that includes:
a reservoir containing the fluid;
a plunger configured to displace the fluid into and out of the reservoir, wherein the plunger is connected to a drive screw; and
an engagement member configured to engage with the drive screw, wherein prior to connection of the reusable part and the disposable part, the engagement member is disengaged from the drive screw allowing the drive screw to freely move within the engagement member;
positioning a free end of the drive screw within a receiving portion in the reusable part; and
connecting the reusable part with the disposable part, wherein, upon connection, the engagement member engages with the drive screw such that upon rotation of the engagement member, the drive screw and the plunger are linearly displaced to deliver fluid contained with the reservoir.

2. A fluid delivery device comprising:
a disposable part including a reservoir and a plunger positioned within the reservoir and connected to a non-rotating drive screw;
an engagement member having a body portion with external teeth, the body portion configured to engage with the drive screw; and
a reusable part including a motor, one or more gears, and a receiving portion driven by at least one of the motor and the one or more gears,
wherein:
the receiving portion is configured to receive the drive screw and engage with the engagement member;
the external teeth of the engagement member engage with inner teeth of the receiving portion; and
upon connection of the reusable part and the disposable part, the engagement member engages with the drive screw and rotation of at least one of the motor and the one or more gears results in rotation of the engagement member to linearly displace the drive screw and the plunger to deliver fluid contained within the reservoir.

3. A fluid delivery device comprising:
a reusable part including a motor and one or more gears;
a disposable part including a reservoir and a plunger positioned within the reservoir and connected to a non-rotating drive screw; and
an engagement member configured to engage with the drive screw,
wherein upon connection of the reusable part and the disposable part, the engagement member engages with the drive screw and rotation of at least one of the motor and the one or more gears results in rotation of the engagement member to linearly displace the drive screw and the plunger to deliver fluid contained within the reservoir.

4. The device according to claim 3, wherein upon connection of the reusable part and the disposable part, the engagement member is positioned within the disposable part.

5. The device according to claim 3, wherein the drive screw is configured to freely move within the engagement member when the engagement member is disengaged from the drive screw.

6. The device according to claim 3, wherein the engagement member includes internal threads that correspond to external threads of the drive screw, wherein upon engagement of the engagement member with the drive screw, the internal threads of the engagement member engage with the external threads of the drive screw.

7. The device according to claim 3, wherein the drive screw is rigidly connected to the plunger.

8. The device according to claim 3, wherein the drive screw is integral with the plunger.

9. The device according to claim 3, wherein the drive screw includes a conical or a hat-shaped tip.

10. The device according to claim 3, wherein the disposable part further comprises an exit port in fluid communication with the reservoir, wherein the exit port is configured to enable filling of the reservoir with fluid via the exit port by pulling the drive screw with the plunger outwardly from the reservoir when the engagement member is disengaged from the drive screw.

11. The device according to claim 3, wherein the device is skin-securable.

12. The device according to claim 3, wherein the engagement member comprises a drive nut.

13. The device according to claim 3, wherein the engagement member includes a first section and a second section, wherein one or more gaps exist between the first section and the second section at least when the engagement member is disengaged from the drive screw.

14. The device according to claim 13, wherein upon engagement of the engagement member with the drive screw, at least one of the one or more gaps is narrowed.

15. The device according to claim 13, wherein the first section is hinged to the second section.

16. The device according to claim 13, wherein the first section is detachably connectable to the second section.

17. The device according to claim 13, wherein the engagement member includes at least one latch and one or more corresponding recesses for locking together the first section and the second section.

18. The device according to claim 3, wherein the reusable part further includes a receiving portion driven by at least one of the motor and the one or more gears, wherein the receiving portion is configured to receive the drive screw and engage with the engagement member.

19. The device according to claim 18, wherein engagement of the engagement member with the receiving portion results in engagement of the engagement member with the drive screw.

20. The device according to claim 18, wherein the engagement member comprises a body portion that engages with the receiving portion in the reusable part.

21. The device according to claim 20, wherein the body portion is curved or at least partially conical.

22. The device according to claim 18, wherein the receiving portion comprises a gear portion having outer teeth configured to mesh with teeth of the one or more gears.

23. The device according to claim 22, wherein the receiving portion further comprises an elongated portion.

* * * * *